US009400264B2

(12) United States Patent
Yamamoto et al.

(10) Patent No.: US 9,400,264 B2
(45) Date of Patent: Jul. 26, 2016

(54) ULTRASONIC TEST EQUIPMENT AND EVALUATION METHOD THEREOF

(71) Applicant: Kabushiki Kaisha Toshiba, Tokyo (JP)

(72) Inventors: Setsu Yamamoto, Yokohama (JP); Jun Semboshi, Yokohama (JP); Masahiro Yoshida, Chigasaki (JP); Takahiro Miura, Yokohama (JP); Kazumi Watanabe, Yokohama (JP); Makoto Ochiai, Yokohama (JP); Satoshi Nagai, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 338 days.

(21) Appl. No.: 14/184,874

(22) Filed: Feb. 20, 2014

(65) Prior Publication Data

US 2014/0230556 A1 Aug. 21, 2014

(30) Foreign Application Priority Data

Feb. 20, 2013 (JP) ................................. 2013-031456

(51) Int. Cl.
*G01N 29/34* (2006.01)
*G01N 29/04* (2006.01)
*G01N 29/44* (2006.01)
*G01N 29/46* (2006.01)

(52) U.S. Cl.
CPC ............ *G01N 29/348* (2013.01); *G01N 29/043* (2013.01); *G01N 29/4427* (2013.01); *G01N 29/46* (2013.01); *G01N 2291/02491* (2013.01)

(58) Field of Classification Search
CPC ............ G01N 29/043; G01N 29/4427; G01N 29/348; G01N 29/46; G01N 2291/02491
USPC .......................................................... 73/602
See application file for complete search history.

(56) References Cited

U.S. PATENT DOCUMENTS

| | | | | |
|---|---|---|---|---|
| 5,309,765 A | * | 5/1994 | Horigome | G01N 29/11 73/602 |
| 5,824,908 A | * | 10/1998 | Schindel | G01N 29/11 73/598 |
| 5,983,701 A | * | 11/1999 | Hassani | G01N 3/307 73/12.01 |
| 6,606,909 B2 | * | 8/2003 | Dubois | G01N 29/0645 73/579 |
| 2004/0227414 A1 | * | 11/2004 | Gunnerman | B06B 1/0261 310/26 |

FOREIGN PATENT DOCUMENTS

| | | |
|---|---|---|
| JP | 2004-340807 | 12/2004 |
| JP | 2005-315636 | 11/2005 |

* cited by examiner

*Primary Examiner* — J M Saint Surin
(74) *Attorney, Agent, or Firm* — Finnegan, Henderson, Farabow, Garrett & Dunner LLP

(57) ABSTRACT

An ultrasonic test equipment includes: a signal generating mechanism that generates a voltage waveform; an ultrasonic transmitting mechanism that excites ultrasonic vibrations having a lower frequency than a predetermined frequency to an object to be tested; an ultrasonic receiving mechanism that receives an ultrasonic response from the object to be tested; an AD converting mechanism that digitizes the received ultrasonic waveform; an analyzing mechanism that performs frequency analysis of the digital ultrasonic waveform digitized by the AD converting mechanism; an evaluating mechanism that extracts a variation of a nonlinear ultrasonic component from a frequency component of the digital ultrasonic wave obtained by the frequency analysis, compares the variation with defect data information in a defect information database, identifies a physical quantity of defect information of the object to be tested, and evaluates a defect in the object to be tested; and a control mechanism that partly or entirely controls a measurement system.

15 Claims, 26 Drawing Sheets

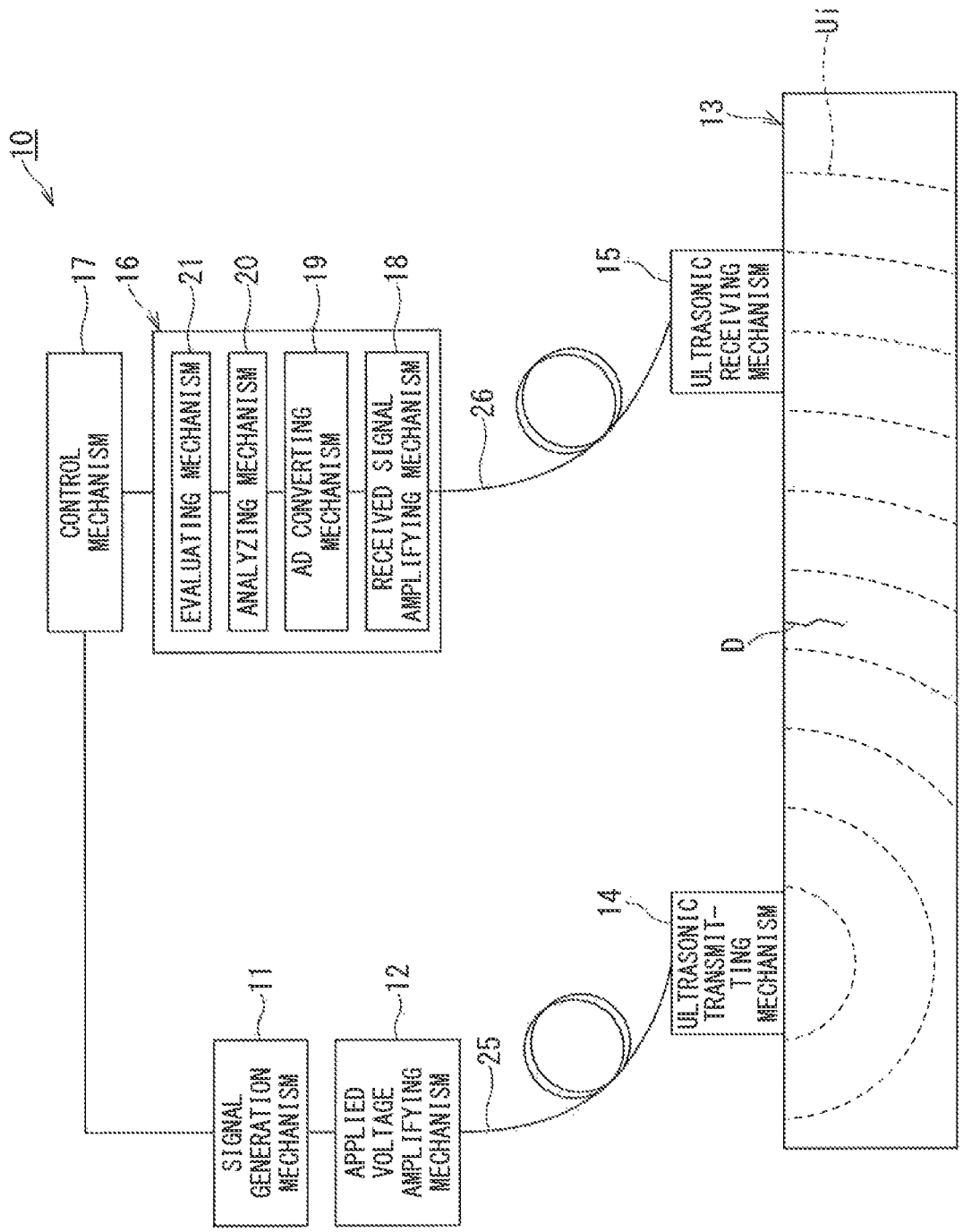
F I G. 1

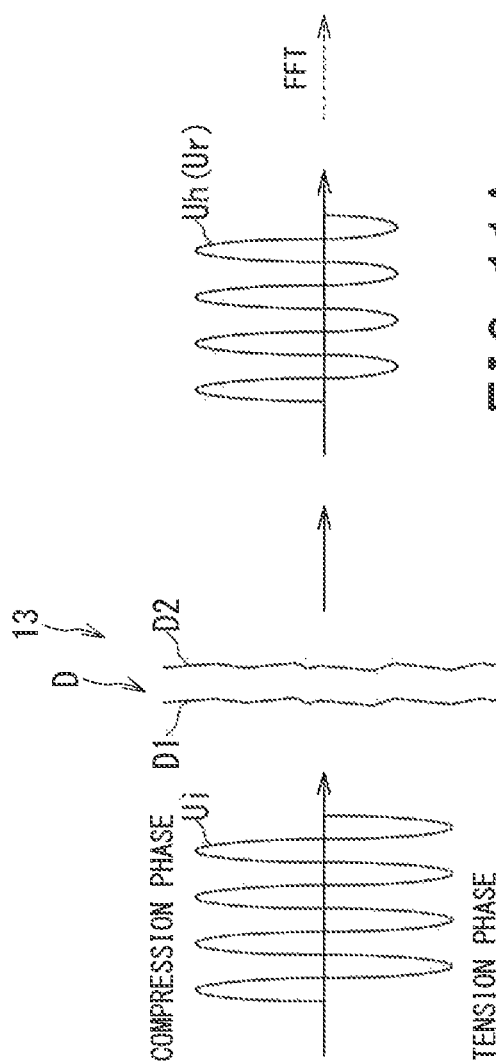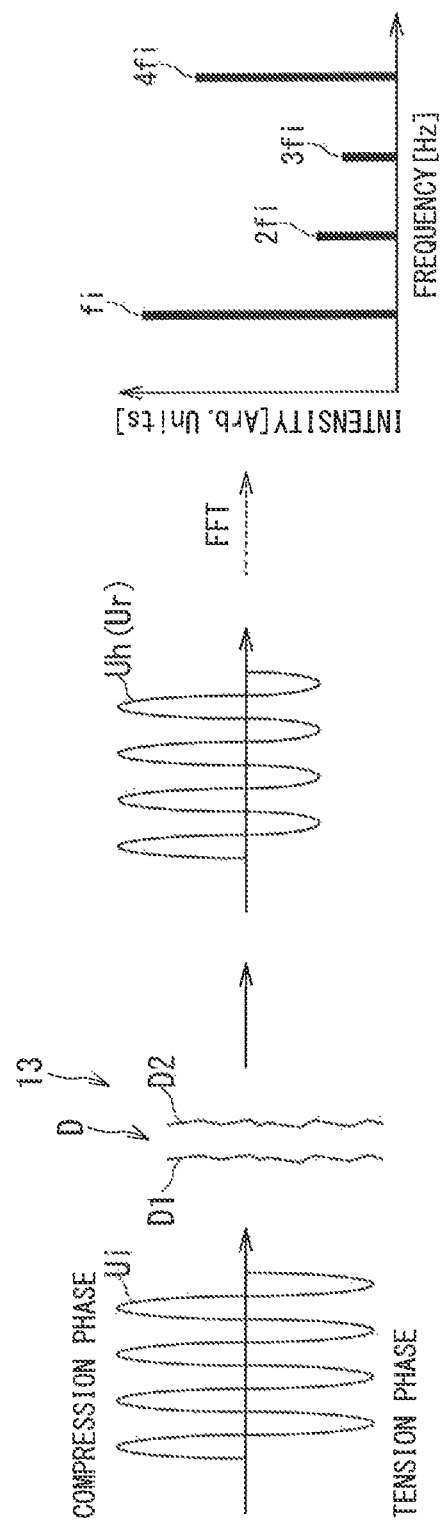
FIG. 11A
FIG. 11B

ULTRASONIC TEST EQUIPMENT AND EVALUATION METHOD THEREOF

BACKGROUND OF THE INVENTION

1. Field of the Invention

The present invention relates to an ultrasonic test equipment capable of performing flaw detection in a wide range of an object to be tested, and an evaluation method for evaluating the tested result.

2. Related Art

Ultrasonic testing is a technique for nondestructively confirming soundness of a surface and an inner portion of a structural material that is an object to be tested, and is an indispensable testing technique in various fields. Particularly, in recent years, there is a demand for testing of a spot where ultrasonic testing has never been required in order to ensure safety of a plant structural object or the like. According to such demand, an improvement in efficiency as well as reliability is being required in the ultrasonic testing.

Radiographic testing (RT) and ultrasonic testing (UT) are listed up as effective techniques for accurate sizing of a volume defect existing in a structural object. The RT is effectively used for detecting a defect with a volume, such as a hole, that exists in a structural object, but not suitable for detecting a defect with no volume, such as a crack and a peel-off. Since the RT includes testing steps such as exposure and development, the improvement in efficiency is limited.

On the other hand, the UT is highly applicable to detection of not only a hole within a structural object, but also a plane defect such as a crack and a peel-off. A test result can be also acquired in real time.

The UT generally uses a monocular probe. Recently, phased array ultrasonic testing (PAUT) technology capable of forming any waveform by emitting ultrasonic waves at shifted timings (delay time) from a plurality of small piezoelectric elements arranged in an array probe becomes practically usable. The UT is thus applied to more and more fields. Among the testing techniques for confirming the soundness of a surface and an inner portion of a structural object, the UT is considered to be most suitable for improving the efficiency.

Improving the efficiency in the testing technique means a decrease in test time in total. The decrease in test time is achieved by decreasing a test time per measurement point, and increasing a test range per measurement point. The test time per measurement point depends on a repetition frequency and a signal processing speed of a flaw detection apparatus, and a scanning speed of a probe. The flaw detection apparatus generally has a repetition frequency of 1 kHz or more and also has a signal processing speed according to the repetition frequency. The scanning speed of the probe largely differs depending on an object to be tested or a testing method. It is thus difficult to discuss an increase in the scanning speed in general terms.

The test range per measurement point that involves the improvement in the efficiency in the testing technique is now described. The ultrasonic testing (UT) utilizes a phenomenon of reflection or diffraction caused by an ultrasonic wave entering a defect or the like. In the UT, it is essential that the entering ultrasonic wave and a signal derived from the defect can be temporally or spatially decomposed. The UT means that a frequency band of an order where directionality can be maintained and the defect can be evaluated by use of temporal information is used (the UT uses a frequency band of about 0.5 MHz to 10 MHz for a typical structural material).

In this case, a range tested at a time in the UT depends on the size of an ultrasonic probe. A monocular probe generally has a maximum diameter of 2 inches. If the probe size is simply increased, its resolution is deteriorated, and thus, the increase in the probe to a larger size is not suitable for practical use in flaw detection of a structural object or the like.

In the PAUT, when the number of sensors is endlessly increased, a test range is also increased. However, the array probe has a larger volume, and thus, the handling thereof becomes difficult. It also becomes necessary to process numerous signals, to place a larger load on hardware such as an ultrasonic flaw detector. The area of the test range may be made larger by increasing one channel of each element of the array probe. However, it becomes difficult to control a beam when the elements are spaced at a pitch more than half the wavelength. It is thus not practical to increase one channel of each element.

Accordingly, even in the PAUT, the range tested at a time is limited to an area of several thousand $mm^2$. The increase in the test range has a limit in the PAUT itself.

In addition to the approaches of increasing the number of sensors and increasing the sensor diameter, there are provided, as a method for increasing the test range of a structural object, a method of using a wave in a different mode from a volume wave, such as a longitudinal wave and a traverse wave, used in the above ultrasonic flaw detection, and a method of simply reducing a frequency to increase a range to which a volume wave reaches.

Flaw detection using a guided wave or a surface wave is a representative example of the former ultrasonic flaw detection. Basically, flaw detection using a surface wave is targeted on only a defect existing in an object surface. Therefore, information regarding a defect inside a structural material or a crack depth cannot be obtained. Although flaw detection using a guided wave basically uses a variety of waves ranging from a plate wave such as a Lamb wave to a surface wave, a defect existing at a certain depth in a thick plate that is an object to be tested cannot be effectively detected.

By using the latter method of reducing a frequency to increase the volume wave reaching range, ultrasonic waves can be caused to propagate through an inner portion of a structural material that is an object to be tested as well as a surface of the structural material. However, defect detection sensitivity is deteriorated along with the decrease in frequency.

Thus, a nonlinear frequency component (response of 2f, 3f, and so on, up to nf, or f/2, f/3, and so on, up to f/n to an incident frequency f) generated from a crack portion by increasing a displacement amplitude of an ultrasonic wave and thereby inducing an opening and closing behavior in the crack portion has attracted attention. The nonlinear component is generated only from a defect in a structural material such as a crack. Thus, the nonlinear component could be applied to accurate detection or evaluation of a defect, material deterioration measurement, or the like. An ultrasonic testing technique for nondestructively detecting a defect in a contact interface of an object to be tested (a structural object) has been disclosed in Patent Document 1 (Japanese Patent Laid-Open No. 2004-340807) or the like. An ultrasonic testing technique for enabling accurate detection or sizing of a closed crack that cannot be detected in normal ultrasonic testing by use of a nonlinear ultrasonic wave is disclosed in Patent Document 2 (Japanese Patent Laid-Open No 2005-315636).

The ultrasonic testing technique disclosed in Patent Document 1 is a testing technique for qualitatively detecting a micro-defect in a contact interface of a structural material (object). The ultrasonic testing technique is effective only in detecting the defect in a contact surface of a structural material, and is not used for quantitative evaluation of a defect size.

In the ultrasonic testing technique disclosed in Patent Document 2, depth information of a defect is acquired and evaluated by using a frequency band in use and temporal axis information. In terms of a test range, it is difficult to increase the test range. The ultrasonic testing technique cannot detect a flaw in a wide range as in the conventional ultrasonic testing.

SUMMARY OF THE INVENTION

The present invention was made in consideration of the circumstances mentioned above, and an object thereof is to provide an ultrasonic test equipment and an evaluation method for evaluating the test result by using a low-frequency and a nonlinear ultrasonic wave to thereby detect a defect of an object to be tested in a wide positional range and obtain physical information such as length and depth of the defect.

The above and other objects can be achieved according to an embodiment of the present invention by providing an ultrasonic test equipment includes: a signal generating mechanism that generates a voltage waveform; an ultrasonic transmitting mechanism that excites ultrasonic vibrations having a lower frequency than a predetermined frequency to an object to be tested; an ultrasonic receiving mechanism that receives an ultrasonic response from the object to be tested; an AD converting mechanism that digitizes the received ultrasonic waveform; an analyzing mechanism that performs frequency analysis of the digital ultrasonic waveform digitized by the AD converting mechanism; and an evaluating mechanism that extracts a variation of a nonlinear ultrasonic component from a frequency component of the digital ultrasonic wave obtained by the frequency analysis, compares the variation with defect data information in a defect information database, identifies a physical quantity of defect information of the object to be tested, and evaluates a defect in the object to be tested; and a control mechanism that partly or entirely controls a measurement system.

According to another embodiment of the present invention, there is also provided a method for evaluating a test result by an ultrasonic test equipment, which includes the steps of: transmitting an ultrasonic wave having a low frequency lower than a predetermined frequency to an object to be tested; receiving an ultrasonic response from the object to be tested by an ultrasonic receiving mechanism; converting the received analog ultrasonic waveform to a digital ultrasonic waveform; performing frequency analysis of the converted digital ultrasonic waveform by an analyzing mechanism; and extracting a variation of a nonlinear ultrasonic component from frequency information of the digital ultrasonic waveform of the object to be tested obtained by the frequency analysis, matching the variation with known defect data information in a defect information database, identifying a physical quantity of defect information of the object to be tested, and then, evaluating a defect in the object to be tested by an evaluating mechanism.

According to a further embodiment of the present invention, there is also provided an ultrasonic test equipment including: a signal generating mechanism that generates a voltage waveform; an ultrasonic transmitting mechanism that excites ultrasonic vibrations having a lower frequency than a predetermined frequency to an object to be tested; an ultrasonic receiving mechanism that receives an ultrasonic response from the object to be detected; an AD converting mechanism that digitizes the received ultrasonic waveform; a calculating mechanism that performs an inverse problem calculation of a spatial intensity distribution from the digitized ultrasonic waveform; a filtering mechanism that calculates the spatial intensity distribution filtered by any frequency component; a variation extracting mechanism that extracts an intensity variation of a nonlinear ultrasonic component; a display mechanism that displays at least the filtered spatial intensity distribution from the filtering mechanism; and a control mechanism that partly or entirely controls a measurement system.

According to the above embodiments of the present invention, by using low-frequency wave and nonlinear ultrasonic wave, a defect of an object to be tested can be detected in a wide range, and information of length and depth of the defect can be obtained.

BRIEF DESCRIPTION OF THE DRAWINGS

FIG. 1 is a basic configuration diagram illustrating a first embodiment of an ultrasonic test equipment according to the present invention;

FIGS. 11A and 11B are explanatory views for respectively explaining examples of generation efficiencies of nonlinear components generated by different defect portions existing in the object to be tested;

FIG. 17 including

17A shows an example in which a chirp wave is used in a signal generating mechanism, and FIG. 17B shows an example in which a mixed wave is used in the signal generating mechanism;

DESCRIPTION OF THE PREFERRED EMBODIMENT

Figure 2:
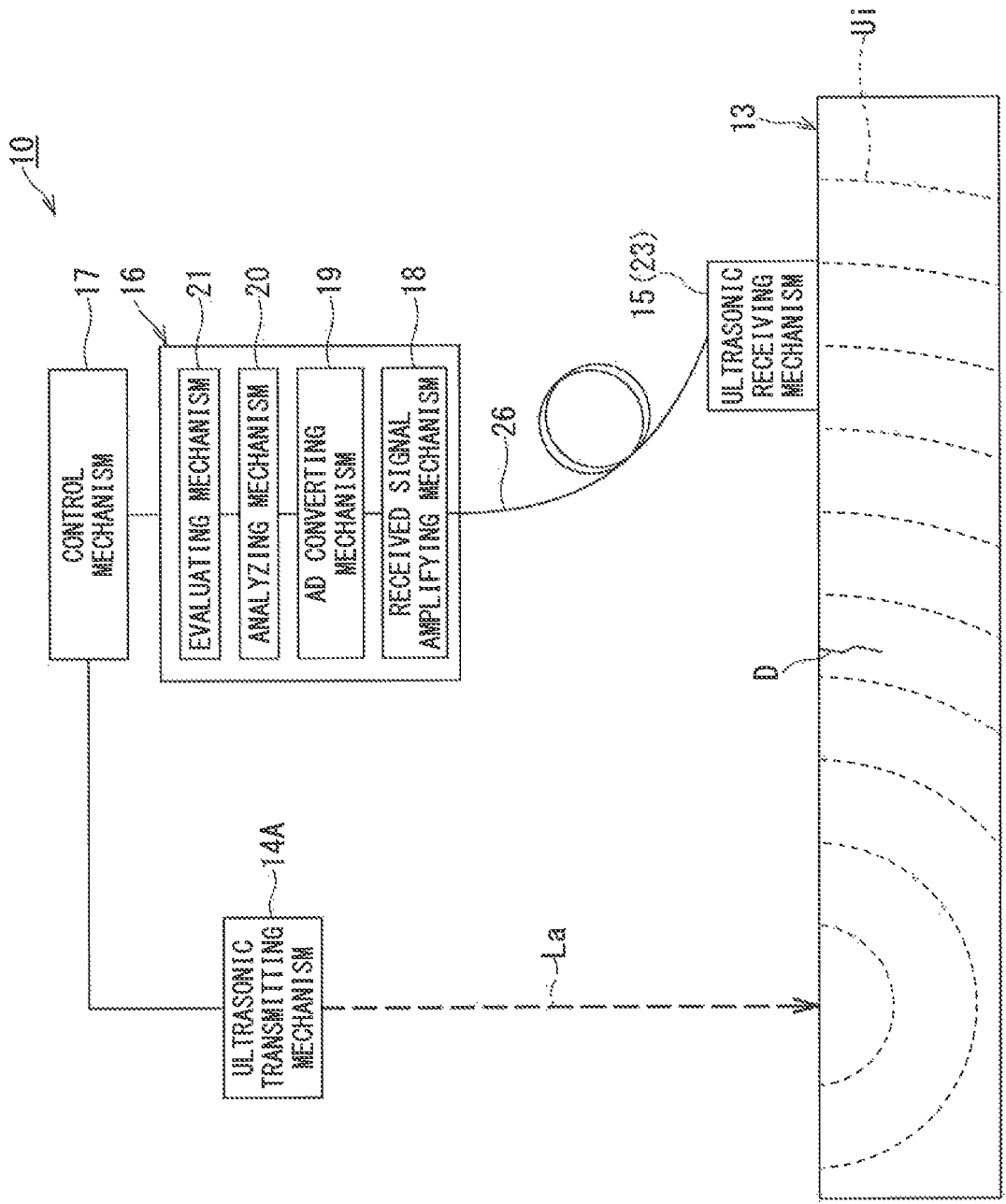
FIG. 2 is a configuration diagram illustrating a first modification of the first embodiment of the ultrasonic test equipment.

Hereunder, embodiments according to the present invention will be described with reference to the accompanying drawings.

First Embodiment

FIG. 1 represents a first embodiment of an ultrasonic test equipment and is a configuration diagram illustrating a representative structural example of an ultrasonic test equipment which can nondestructively and extensively detect a defect (a volume defect) in a surface and an inner portion of an object to be tested, and which can also acquire defect information such as a position, a length, a depth, and an opening width of the defect.

An ultrasonic test equipment 10 includes a signal generating mechanism 11 that generates a voltage waveform upon receiving a voltage from a power source, not shown, an applied voltage amplifying mechanism 12 which changes an amplitude of the generated voltage waveform, an ultrasonic transmitting mechanism 14 that excites and transmits ultrasonic vibrations to a wide range of an object to be tested 13, an ultrasonic receiving mechanism 15 that receives an ultrasonic response from the object to be tested 13, a signal processor 16 that processes the received ultrasonic signal and acquires position, length, and depth information of a defect in the object to be tested 13 that is a structural object, and a control mechanism 17 that partly or entirely controls a measurement system.

The signal processor 16 includes a received signal amplifying mechanism 18 that amplifies the analog ultrasonic (waveform) signal received by the ultrasonic receiving mechanism 15, an AD converting mechanism 19 that digitizes the amplified analog ultrasonic signal, an analyzing mechanism 20 that performs frequency analysis of the digital ultrasonic waveform digitized by the AD converting mechanism 19, and an evaluating mechanism 21 that extracts a variation of a nonlinear ultrasonic component from a frequency component of the digital ultrasonic wave obtained by the frequency analysis, compares and matches the variation with known defect data information in a defect information database, and identifies the defect information (the position, length, depth, opening width or the like of the defect) of the object to be tested 13.

In addition to the controlling of the measurement system by synchronizing measurement system constituent elements of the ultrasonic test equipment 10, the control mechanism 17 includes a user interface and a display unit that enable a user to control the system. The control mechanism 17 can also easily change setting values, check measurement results, or the like. Further, although the control mechanism 17 can partly or entirely control the system, the respective constituent elements may be adjusted and driven separately and independently.

The signal generating mechanism 11 of the ultrasonic test equipment 10 is operationally controlled in a digital or analog manner by the control mechanism 17 to output the voltage waveform of an analog voltage signal. The analog voltage waveform may have a basic shape such as sinusoidal, rectangular, sawtooth, or triangular.

In addition to the output waveforms, a chirp waveform whose frequency continuously changes, an M-sequence waveform whose frequency randomly changes, a mixed waveform having a plurality of different frequencies, or any other waveforms may be employed. The output waveform may be transmitted at any wavenumber of a pulse wave, a continuous wave, and a burst wave. The signal generating mechanism 11 needs to have at least one output system. A plurality of signal generating mechanisms 11 may be employed to constitute the system of the ultrasonic test equipment 10.

The applied voltage amplifying mechanism 12 that amplifies the signal having the voltage waveform generated by the signal generating mechanism 11 can amplify the voltage waveform to any intensity. The applied voltage amplifying mechanism 12 may be configured to separate the applied voltage of the input voltage waveform by a time window, or partially increase (amplify) the intensity to amplify voltage waveform signals from a plurality of systems. The applied voltage amplifying mechanism 12 may be configured to amplify analog voltage waveform signals from a plurality of systems. The signal generating mechanism 11 and the applied voltage amplifying mechanism 12 are configured separately as shown in FIG. 1, but they may be also incorporated in one unit.

The amplified voltage waveform signal is input to the ultrasonic transmitting mechanism 14. The ultrasonic transmitting mechanism 14 excites and oscillates ultrasonic waves with a low frequency and a large amplitude. The ultrasonic transmitting mechanism 14 may have any configuration including a piezoelectric element capable of generating ultrasonic waves by an piezoelectric effect of ceramics, a composite material, or any other materials, a piezoelectric element of a polymer film, or any other mechanisms capable of generating ultrasonic waves, a dumping material that dumps ultrasonic waves, and a front surface plate that is attached to an oscillation surface of ultrasonic waves, or a configuration composed of a combination of the components mentioned above.

The ultrasonic transmitting mechanism 14 is composed of an electromagnetic or piezoelectric ultrasonic transducer, in the ultrasonic transducer, an actuator having a magnetostriction effect or the like may be used as an ultrasonic generating mechanism.

As a first modification of the first embodiment, a laser-ultrasonics for casting a pulsed laser beam La onto the surface of the object to be tested 13 to excite an elastic wave may be used as an ultrasonic transmitting mechanism 14A as shown in FIG. 2 instead of the combination of the signal generating mechanism 11, the applied voltage amplifying mechanism 12, and the ultrasonic transmitting mechanism 14. Examples of the laser used herein include a Nd:YAG laser, a $CO_2$ laser, an Er:YAG laser, a titanium-sapphire laser, an alexandrite laser, a ruby laser, a dye laser, and an excimer laser. Of course, a laser light source other than those described above may be employed.

Figure 3:
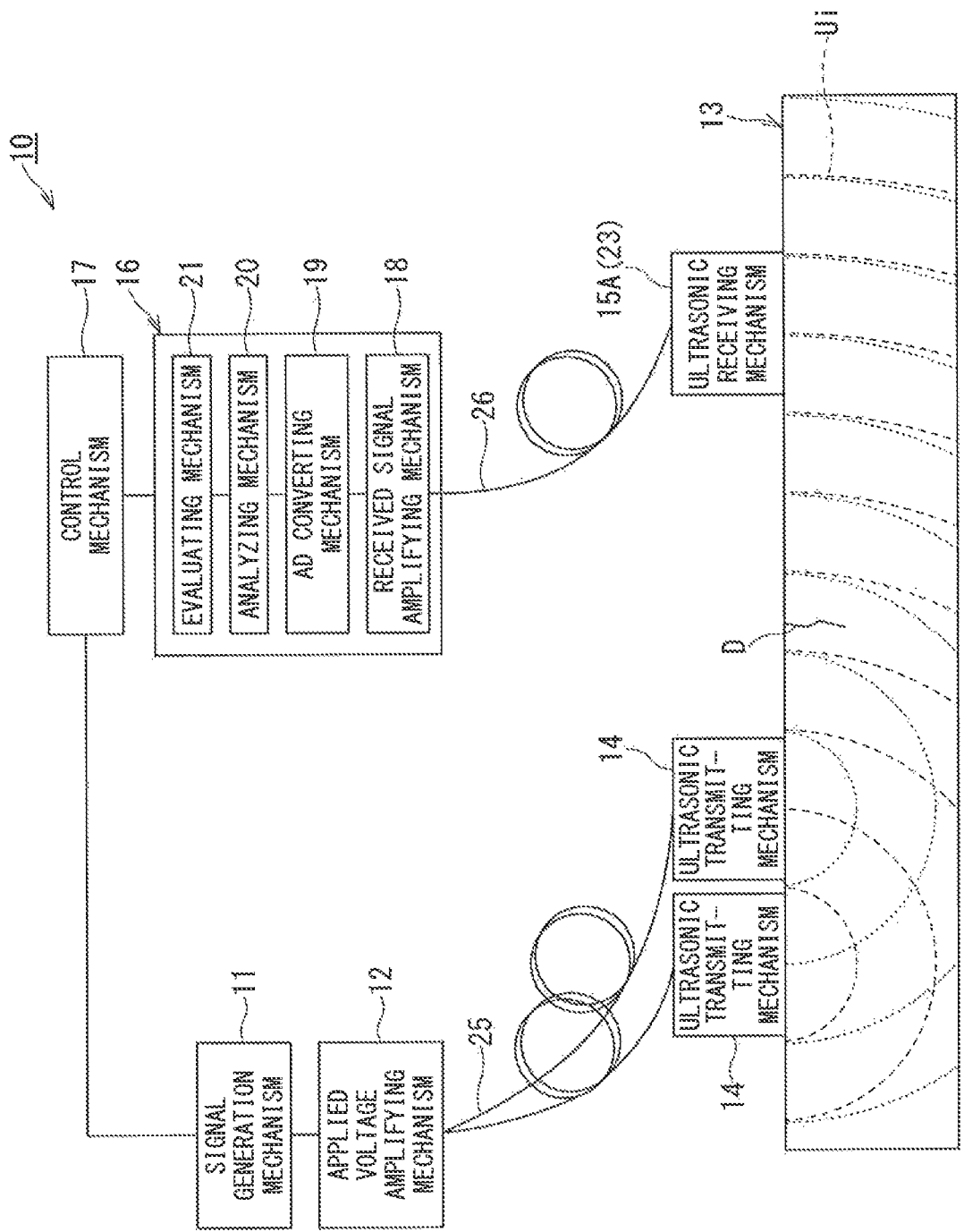
FIG. 3 is a configuration diagram illustrating a second modification of the first embodiment of the ultrasonic test equipment.

As a second modification of the first embodiment, the ultrasonic test equipment 10 may also include a plurality of ultrasonic transmitting mechanisms 14 as shown in FIG. 3. An ultrasonic receiving mechanism 15A may be composed of an ultrasonic transducer, or any other devices capable of receiving ultrasonic waves. A so-called ultrasonic probe 23 having any configuration including a piezoelectric element capable of generating ultrasonic waves by an piezoelectric effect of ceramics, a composite material, or any other materials, a piezoelectric element of a polymer film, or any other mechanisms capable of receiving ultrasonic waves, a dumping material that dumps ultrasonic waves, and a front surface plate that is attached to an oscillation surface of ultrasonic waves, or a configuration composed of a combination of the above components may be also used. A Langevin type transducer, or an actuator having a magnetostriction effect may be used as an ultrasonic generating mechanism.

Figure 4:
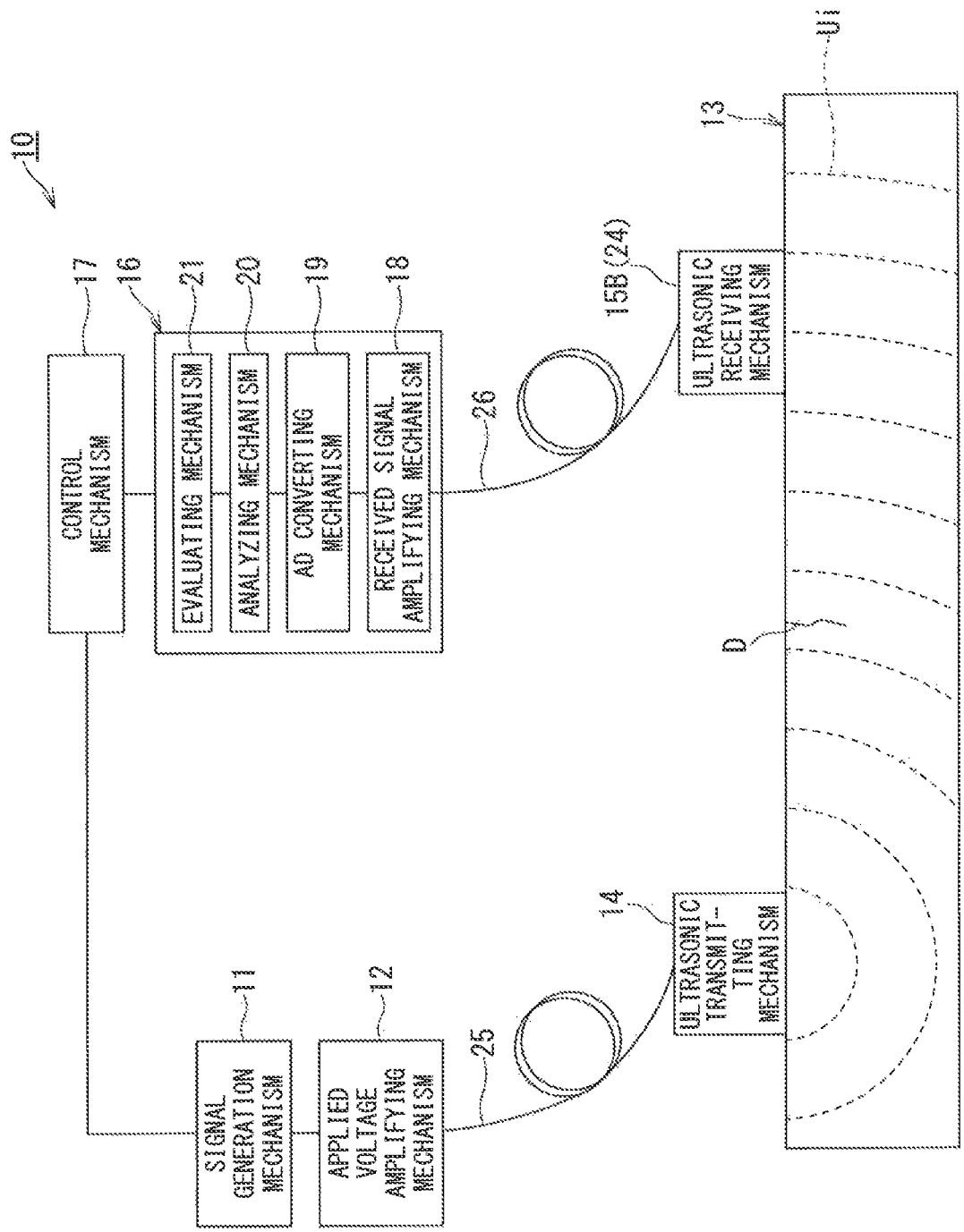
FIG. 4 is a configuration diagram illustrating a third modification of the first embodiment of the ultrasonic test equipment.

As a third modification of the first embodiment, a laser interferometer 24 or a vibration meter that casts a laser beam Lb to the object to be tested 13 and observes a Doppler shift may be used for an ultrasonic receiving mechanism 15B in the ultrasonic test equipment 10 as shown in FIG. 4.

Examples of the laser interferometer 24 include a Michelson interferometer, a homodyne interferometer, a heterodyne interferometer, a Fizeau interferometer, a Mach-Zehnder interferometer, a Fabry-Perot interferometer, and a photorefractive interferometer. Of course, a laser interferometer other than those described above may be employed.

Figure 5:
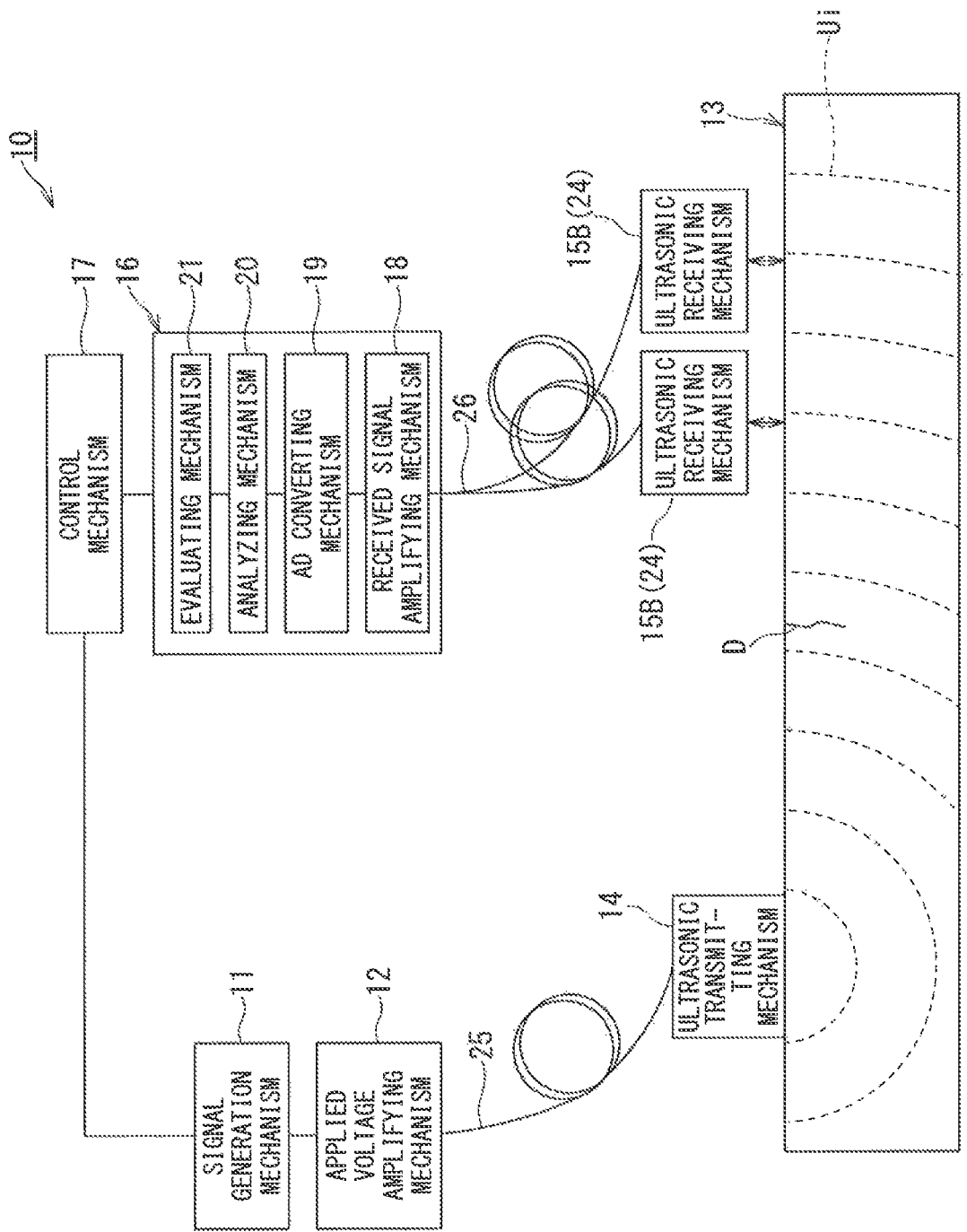
FIG. 5 is a configuration diagram illustrating a fourth modification of the first embodiment of the ultrasonic test equipment.

Moreover, as a fourth modification of the first embodiment, the ultrasonic receiving mechanism 15B may perform measurement using a knife-edge method as a measurement method other than the measurement using the laser interferometer 24 in the ultrasonic test equipment 10 as shown in FIG. 5. In this case, a plurality of ultrasonic receiving mechanisms 15B and 15B are used to perform measurement.

The received signal amplifying mechanism 18 constituting the signal processor 16 of the ultrasonic test equipment 10 is a signal amplifier commonly called a preamplifier. The received signal amplifying mechanism 18 may be incorporated in the signal processor 16, or may be configured separately. When the plurality of ultrasonic receiving mechanisms 15B and 15B respectively output ultrasonic signals, the received signal amplifying mechanism 18 can respectively amplify the plurality of received ultrasonic signals.

The AD converting mechanism 19 has a function to digitize the received analog ultrasonic signal that is the analog voltage signal. The AD converting mechanism 19 can also digitize the plurality of analog signals. The plurality of signals can be processed by using a plurality of channels, by using a switch that enables sequential conversion of the plurality of signals, or by using both the channels and the switch.

The analyzing mechanism 20 performs the frequency analysis of the waveform of the digitized ultrasonic signal. The frequency analysis may be performed by a general fast Fourier transform (FFT), a short-time Fourier transform (STFT), a wavelet transform, frequency analysis processing using temporal information such as a Wigner distribution, or any other signal processing.

The evaluating mechanism 21 can extract defect data information having a closest tendency by matching the frequency information obtained from the analyzing mechanism 20 with the known defect data information of test pieces or samples obtained before in the defect information database. The known defect data information obtained at this time corresponds to the defect length, the defect depth, the defect opening width, and a stress state applied to the defect of the object to be tested 13. Various other defect information may be also acquired.

In addition to the controlling of the respective constituent elements of the ultrasonic test equipment 10, the control mechanism 17 of the ultrasonic test equipment 10 includes the user interface and the display unit that enable a user to control the respective constituent elements (system) of the ultrasonic test equipment 10. The control mechanism 17 can also easily change setting values, check measurement results, or the like in the ultrasonic test equipment 10. Further, the control mechanism 17 can partly or entirely control the measurement system (the respective constituent elements) of the ultrasonic test equipment 10, and the respective constituent elements may be adjusted and driven separately and independently, Operation of First Embodiment Hereunder, an operation of the ultrasonic test equipment 10 will be described, in the ultrasonic test equipment 10, when a voltage is applied from the power source, not shown, the signal generating mechanism 11 outputs an analog voltage waveform. The applied voltage waveform output from the signal generating mechanism 11 is amplified to a desired voltage intensity by the applied voltage amplifying mechanism 12. The applied voltage waveform amplified by the applied voltage amplifying mechanism 12 is sent to the ultrasonic transmitting mechanism 14 through a cable 25.

The applied voltage waveform amplified by the applied voltage amplifying mechanism 12 is input into the ultrasonic transmitting mechanism 14. The ultrasonic transmitting mechanism 14 excites an ultrasonic wave with a low frequency and a large amplitude, and oscillates ultrasonic wave having the low-frequency and large-amplitude (hereunder, called "low-frequency and large-amplitude ultrasonic wave"), which is transmitted as an incident ultrasonic wave Ui to the object to be tested 13. The incident ultrasonic wave Ui has a lower frequency of 20 kHz to 1 MHz, and preferably 20 kHz to 100 kHz than a predetermined frequency, and a large amplitude of 50 nm to 10 μm, and preferably 100 nm to 5 μm. In the present embodiment, the object to be tested 13 is a plate material having a thickness of several cm, e.g., 40 mm.

Figure 6:
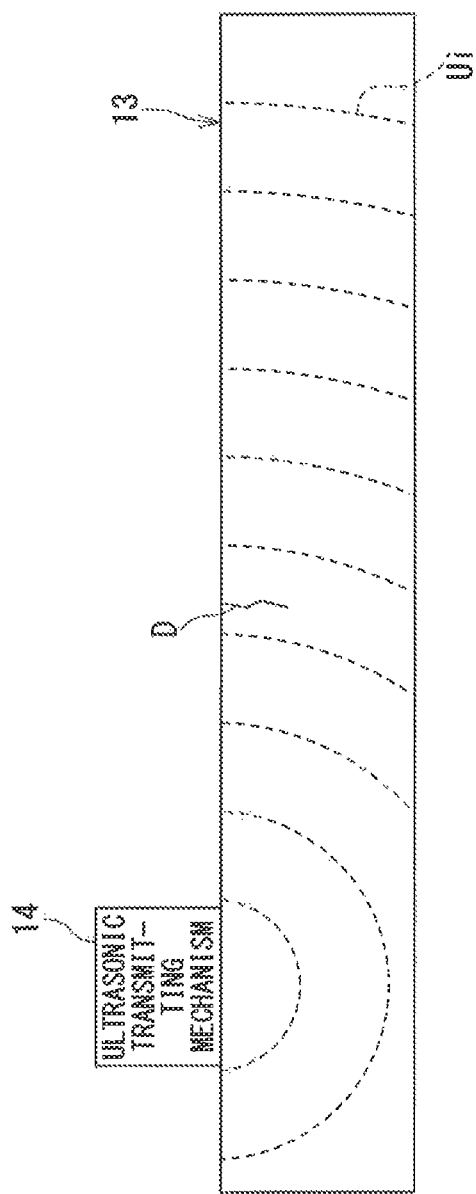
FIG. 6 shows a propagation example of a low-frequency and large-amplitude ultrasonic wave transmitted from an ultrasonic transmitting mechanism of the ultrasonic test equipment.

Since the incident ultrasonic wave Ui oscillated by the ultrasonic transmitting mechanism 14 is a low-frequency and large-amplitude ultrasonic wave, the incident ultrasonic wave Ui has a low directionality and a low propagation attenuation rate as shown in FIG. 6. Since the incident ultrasonic wave Ui entering the object to be tested 13 is a low-frequency and large-amplitude ultrasonic wave, the incident ultrasonic wave Ui propagates in a wide range so as to spread over the entire surface and the entire inner portion of the object to be tested 13.

The propagating incident ultrasonic wave Ui is received as a received ultrasonic wave Ur by the ultrasonic receiving mechanism 15. The analog received ultrasonic wave Ur received by the ultrasonic receiving mechanism 15 is sent to the received signal amplifying mechanism 18 through a cable 26, and amplified therein. The amplified received ultrasonic wave Ur is then sent to the AD converting mechanism 19, where the analog received ultrasonic wave Ur is digitized to be converted to a digital ultrasonic wave. A processable digital ultrasonic waveform signal is thereby obtained.

The digital ultrasonic waveform digitized by the AD converting mechanism 19 is subsequently sent to the analyzing mechanism 20. The analyzing mechanism 20 processes the digital ultrasonic waveform Ur to perform the frequency analysis of the ultrasonic wave. The frequency analysis by the analyzing mechanism 20 may be performed by the general fast Fourier transform (FFT), the short-time Fourier transform (STFT), the wavelet transform, the processing using temporal information such as the Wigner distribution, or any other signal processing.

One example of the signal analysis processing by the analyzing mechanism 20 will be described hereunder.

A distance between the ultrasonic transmitting mechanism 14 and the ultrasonic receiving mechanism 15, a propagation velocity of the ultrasonic wave or the like are already known. Thus, the analyzing mechanism 20 can obtain the position of a defect D existing in the surface or the inner portion of the object to be tested 13 by obtaining a time before the incident ultrasonic wave Ui from the ultrasonic transmitting mechanism 14 reaches the defect D and a time before the ultrasonic wave reaches the ultrasonic receiving mechanism 15 from the defect D, and analyzing the time axis information.

The analyzing mechanism 20 also functions as a position identifying device for identifying the defect position by performing correlation processing on the digital ultrasonic waveform from the AD converting mechanism 19.

Figure 7:
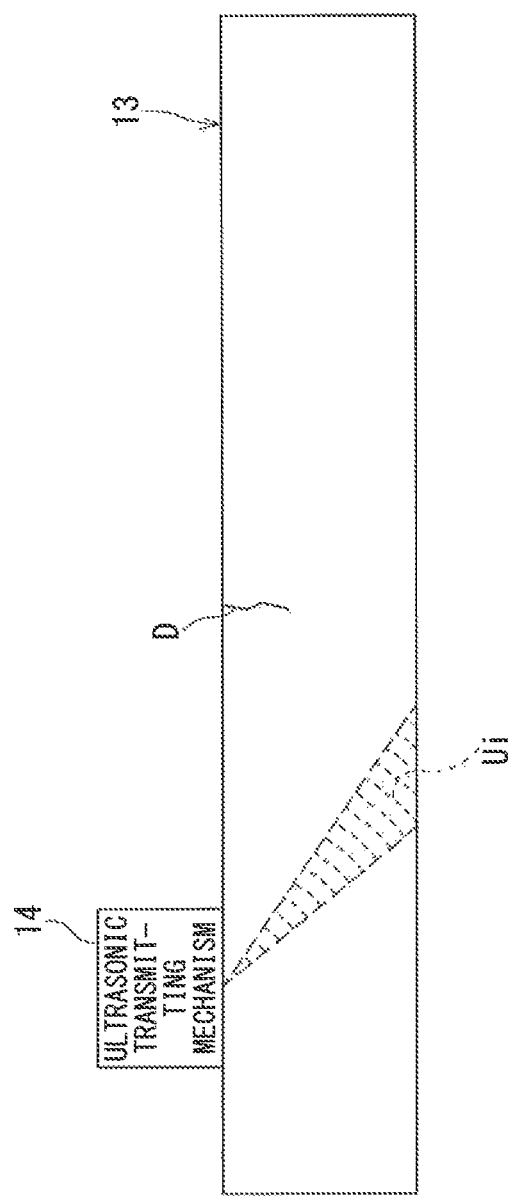
FIG. 7 shows a propagation example of a high-frequency ultrasonic wave transmitted from the ultrasonic transmitting mechanism of the ultrasonic test equipment.

In conventional ultrasonic flaw detection intended for sizing of the object to be tested 13, an ultrasonic wave having a high frequency of 1 MHz to 5 MHz is used. The ultrasonic wave has a high directionality and propagates in a form shown in FIG. 7. Thus, it takes time to search the defect D existing in the object to be tested 13. It is difficult to effectively detect the defect D in the object to be tested 13.

Figure 8:
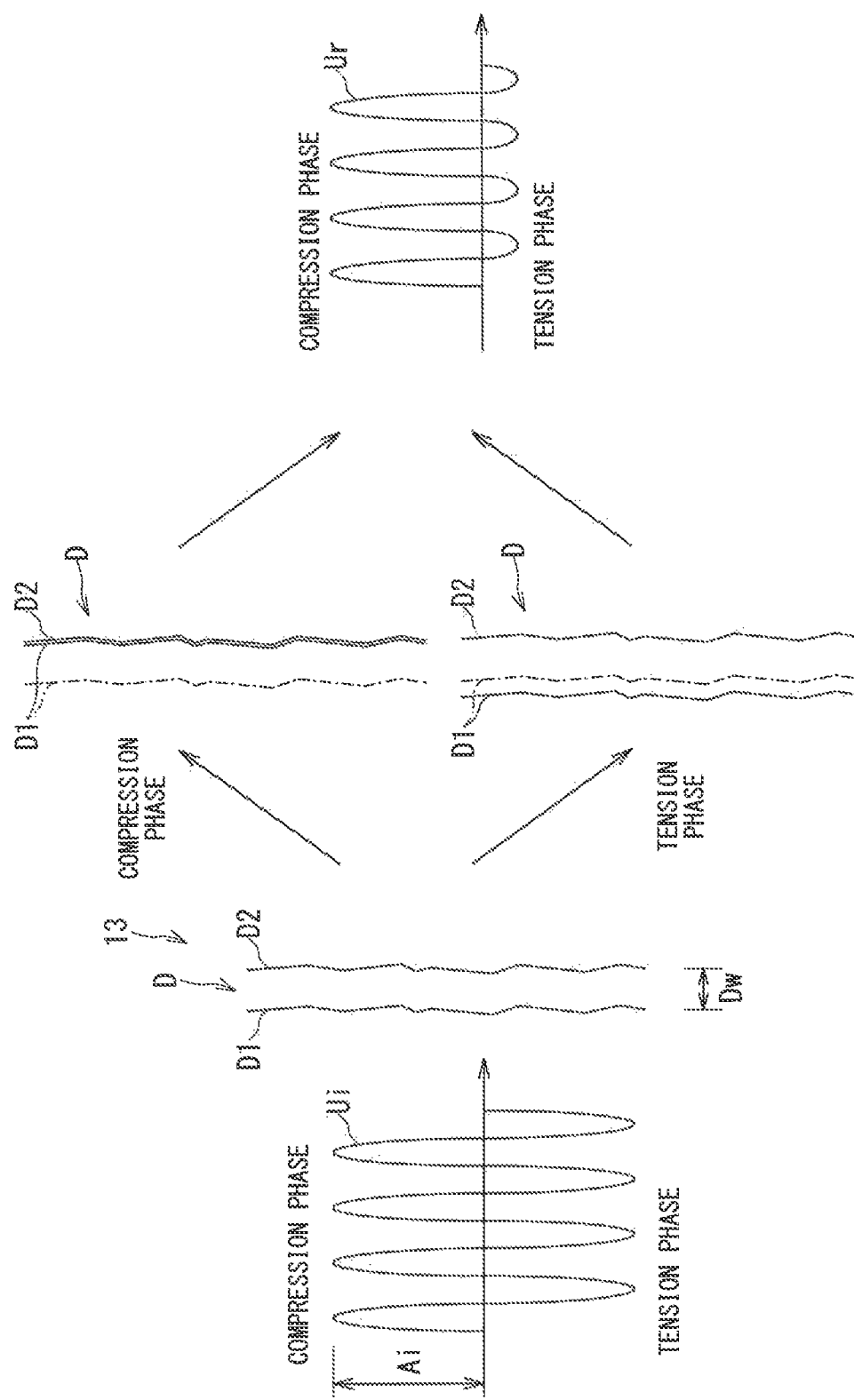
FIG. 8 is an explanatory view illustrating an example of an opening and closing behavior generated by an incident ultrasonic wave in a crack surface of a defect portion in an object to be tested.

The ultrasonic test equipment 10 of the first embodiment uses the low-frequency and large-amplitude ultrasonic wave as the incident ultrasonic wave Ui. The incident ultrasonic wave Ui has a low directionality, propagates in a wide range, and has a low propagation attenuation rate. Thus, the incident ultrasonic wave Ui and the received ultrasonic wave Ur are hardly attenuated. When the defect D exists in the object to be tested 13, the incident ultrasonic wave Ui reaches the defect D to generate an opening and closing behavior called clapping in a crack surface of the object to be tested 13 as shown in FIG. 8 due to the large amplitude of the incident ultrasonic wave Ui.

The incident ultrasonic wave Ui output to the object to be tested 13 is generally represented by a compressional wave as a longitudinal wave. As shown in FIG. 8, a compression phase and a tension phase act on defect interfaces $D_1$ and $D_2$ of the crack surface as the defect D of the object to be tested 13. When the large-amplitude incident ultrasonic wave Ui reaches the defect D, an opening and closing behavior (i.e., clapping) phenomenon in which the defect interfaces $D_1$ and $D_2$ of the crack surface are clapped or rubbed together is caused by the opening and closing behavior such as clapping generated in the defect interfaces $D_1$ and $D_2$ of the defect D in the object to be tested 13.

The opening and closing behavior phenomenon causes an ultrasonic rectification effect in which only the compression phase of the incident ultrasonic wave Ui is transmitted and the tension phase is not transmitted.

In addition to the rectification effect, the opening and closing behavior phenomenon is known to further cause sliding according to a stress state Dp generated in the defect interfaces $D_1$ and $D_2$ due to a shear component acting on the defect interfaces $D_1$ and $D_2$ of the crack surface, or a behavior in which vibrations of one of the defect interfaces $D_1$ or $D_2$ (e.g., the defect interface $D_1$) strike up another of the defect interfaces $D_1$ or $D_2$ (e.g., the defect interface $D_2$).

Figure 9:
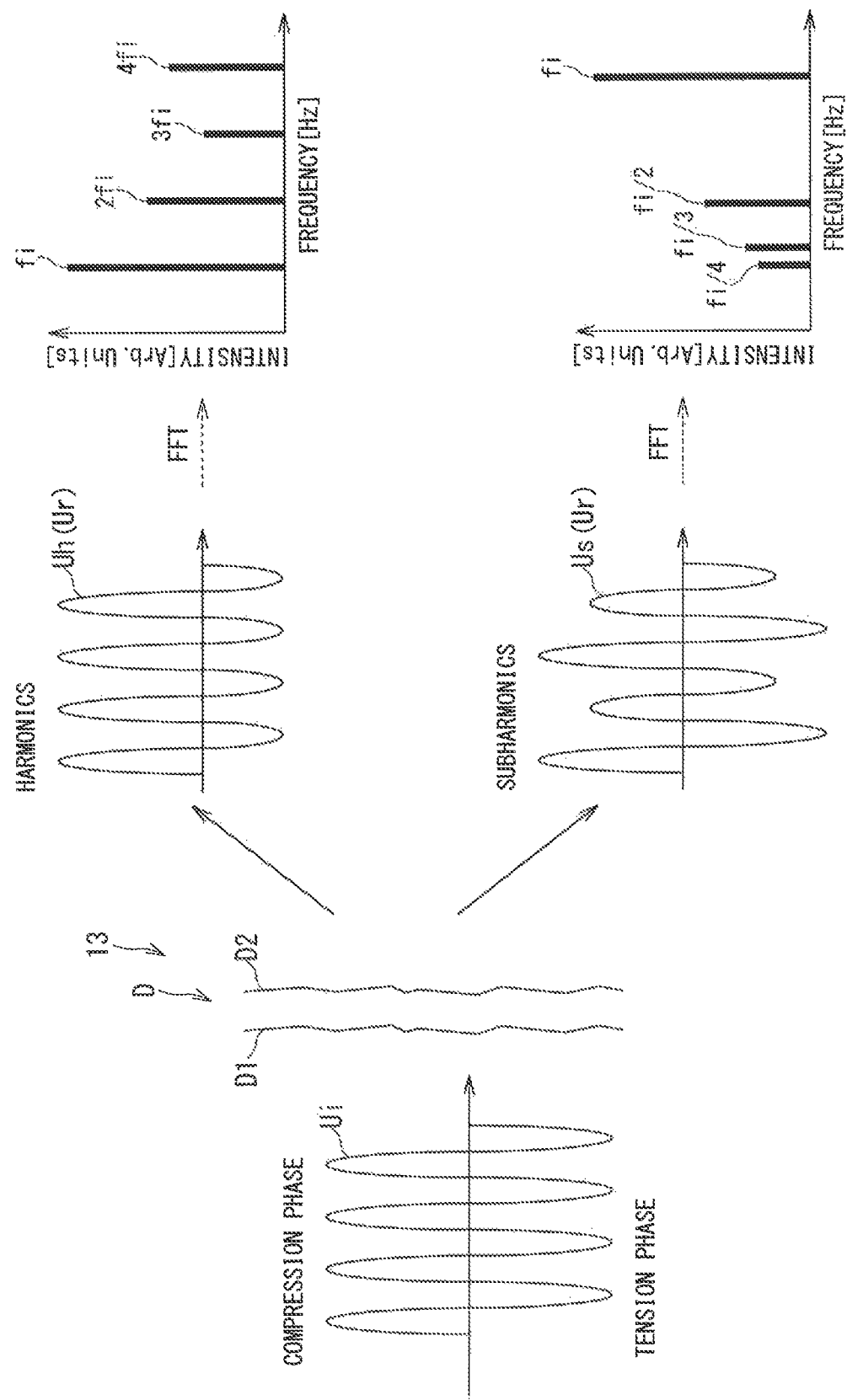
FIG. 9 is an explanatory view illustrating a nonlinear phenomenon by harmonics and subharmonics of the incident ultrasonic wave in the crack surface of the defect portion in the object to be tested.

Due to the opening and closing behavior, the sliding and striking-up behavior phenomena in the defect interfaces $D_1$ and $D_2$ of the crack surface, there occurs a nonlinear phenomenon in which harmonics Uh having a double (second-order) frequency, a triple (third-order) frequency, a quadruple (fourth-order) frequency and so on, up to an n-time (nth-order) frequency of an incident frequency fi of the incident ultrasonic wave Ui, or subharmonics Us having a ½ frequency, a ⅓ frequency, a ¼ frequency and so on, up to a 1/n frequency of the incident frequency fi are generated as shown in FIG. 9.

Further, although the features of the harmonics and the subharmonics are separately shown in FIG. 9, the harmonics and the subharmonics may be generated in a complex manner. The nonlinear phenomenon also occurs within the ultrasonic transmitting mechanism, an interface between the ultrasonic transmitting mechanism 14 and the object to be tested 13, and an acoustic medium. The observed generation efficiency of the nonlinear phenomenon changes depending on the presence of the defect D generated in the object to be tested 13.

Figure 10A:
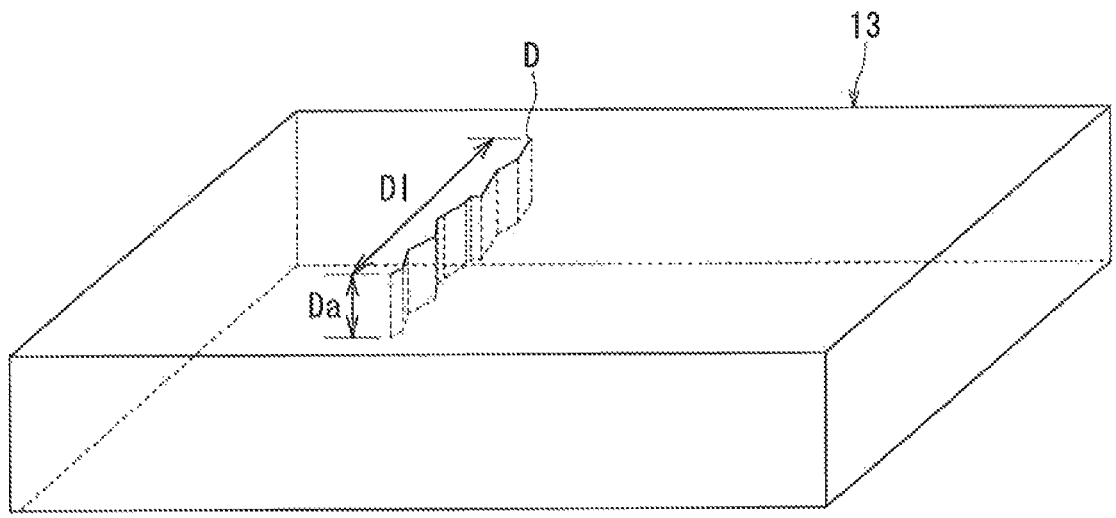
FIG. 10A is an explanatory view of defect information of the defect portion in the object to be tested.
Figure 10B:
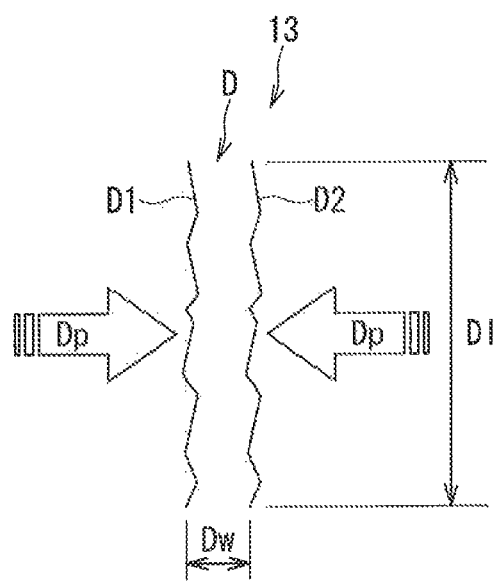
FIG. 10B is a partial upper view of the defect portion in the object to be tested as viewed from an upper side.

When the defect D exists in the object to be tested 13, the generation efficiency of the nonlinear phenomenon by the defect D changes depending on the incident frequency fi and an incident amplitude Ai of the incident ultrasonic wave Ui, a defect length Dl, a defect depth Da, a defect opening width Dw, and the stress state Dp applied to the defect (see FIGS. 10A and 10B).

When the defect D exists in the object to be tested 13, the frequency components of the harmonics of the received ultrasonic wave Ur in the nonlinear phenomenon change as shown in FIGS. 11A and 11B.

The frequency components of the harmonics Uh of the received ultrasonic wave Ur change by the frequency analysis using the fast Fourier transform (FFT). In FIG. 11A that shows one example of the object to be tested 13, scale intensities of the harmonic Uh components on the vertical axis are sequentially decreased from the incident frequency fi to double (second-order) and triple (third-order) frequencies 2fi and 3fi. A quadruple (fourth-order) frequency 4fi has a slightly larger scale intensity than 3fi. Among the frequency components of the harmonics, the double frequency 2fi has a slightly smaller scale intensity than the incident frequency fi, but has a larger scale intensity than the other frequencies 3fi and 4fi.

In FIG. 11B that shows another example of the object to be tested 13, the scale intensities of the harmonic Uh components on the vertical axis are rapidly decreased from the incident frequency fi to the double and triple frequencies 2fi and 3fi. The quadruple frequency 4fi has a larger scale intensity than 3fi.

In the first example in which the object to be tested 13 has the defect D, the frequencies 2fi and 4fi of the second-order and fourth-order harmonics can be both observed as shown in FIG. 11A. In the second example in which the defect length Dl of the defect. D of the object to be tested 13 is half of the above example, the generation efficiency of the frequency 4fi of the fourth-order harmonics is increased as shown in FIG. 11B.

In general, when the defect D existing in the object to be tested 13 has a small size, the second-order frequency 2fi is increased as compared to a case in which the defect D has a large size. When the defect D has a larger size, the fourth-order frequency 4fi tends to be increased.

Based on the analysis tendency obtained by the frequency analysis in the analyzing mechanism 20 of the signal processor 16, the defect size (physical quantity) of the object to be tested 13 can be evaluated.

In the ultrasonic test equipment 10 of the present embodiment, the ultrasonic wave Ur received by the ultrasonic receiving mechanism 15 is amplified to a sensitivity specified by the received signal amplifying mechanism 18, and digitized by the AD converting mechanism 19. The digital ultrasonic waveform is subjected to the frequency analysis in the analyzing mechanism 20, and output as the frequency information derived from the defect in the object to be tested 13.

The analyzing mechanism 20 analyzes the generation efficiency of the nonlinear ultrasonic component from the frequency components of the digital ultrasonic waveform obtained by the AD converting mechanism 19. The frequency information derived from the defect obtained by the frequency analysis in the analyzing mechanism 20 is sent to the evaluating mechanism 21. The known relationship between the defect information of test pieces or samples and the frequency is accumulated so as to constitute the defect information database of the evaluating mechanism 21. The known defect data information (physical quantity) such as the length, depth, and opening width of the defect is accumulated and stored as the defect data information in the defect information database for each test piece or each sample corresponding to the material of the object to be tested 13.

The digital ultrasonic waveform of the object to be tested 13 digitized by the AD converting mechanism 19 is subjected to the frequency analysis in the analyzing mechanism 20, and sent to the evaluating mechanism 21 as the frequency information derived from the defect in the object to be tested 13. The evaluating mechanism 21 matches and compares the frequency information derived from the defect obtained by the frequency analysis with the known defect data information accumulated in the defect information database, and evaluates the frequency information. The evaluating mechanism 21 thereby acquires the defect information of the object to be tested 13, that is, at least one of the physical quantities of the length, depth, opening width, or stress state of the defect. The physical quantity of the defect information of the object to be tested 13 matched and evaluated in the evaluating mechanism 21 is identified, output and displayed on a display device, not shown, and then recorded. The physical quantities such as the length, depth, and opening width of the defect are also stored as the known defect data information in the defect information database in the evaluating mechanism 21.

Effect of First Embodiment

The defect information of the object to be tested 13 obtained in the evaluating mechanism 21 includes the physical quantities such as the defect length Dl, the defect depth Da, the defect opening width (opening amount) Dw, and the stress state Dp applied to the defect D of the object to be tested 13. Therefore, by matching the frequency information derived from the defect in the object 13 obtained by the frequency analysis in the analyzing mechanism 20 with the defect data information in the evaluating mechanism 21, the physical quantity information such as the defect length or defect depth of the object to be tested can be acquired. The physical quantities of the defect D or the like of the object to be tested 13 can be extensively and accurately evaluated in a quantitative manner.

In the ultrasonic test equipment 10 of the present embodiment, the defect D in the object to be tested 13 can be extensively and accurately evaluated and tested in a quantitative manner by using the low-frequency and large-amplitude incident ultrasonic wave Ui. In addition to the evaluation of the defect D in the object 13 by the flaw detection using the low-frequency and large-amplitude ultrasonic wave and performing the physical quantity sizing of the defect, the ultrasonic test equipment 10 can also determine whether or not the defect D has a progressing tendency based on the stress state Dp. For example, when a tensile stress (the tension phase) is applied to the defect D in the object to be tested 13, it is determined that the defect D progresses. When a compressive stress (the compression phase) is applied to the defect D, it is determined that the defect D has a less progressing tendency or no progressing tendency.

In the ultrasonic test equipment 10 of the present embodiment, the crack sizing of the object to be tested 13 can be extensively and accurately evaluated, and the defect in the object 13 can be quantitatively detected by using the low-frequency nonlinear ultrasonic wave which extensively propagates through the object 13, and in which the generation efficiency changes only by the defect D.

Second Embodiment

Next, a second embodiment of the present invention will be described with reference to FIGS. 12 to 14.

Figure 12:
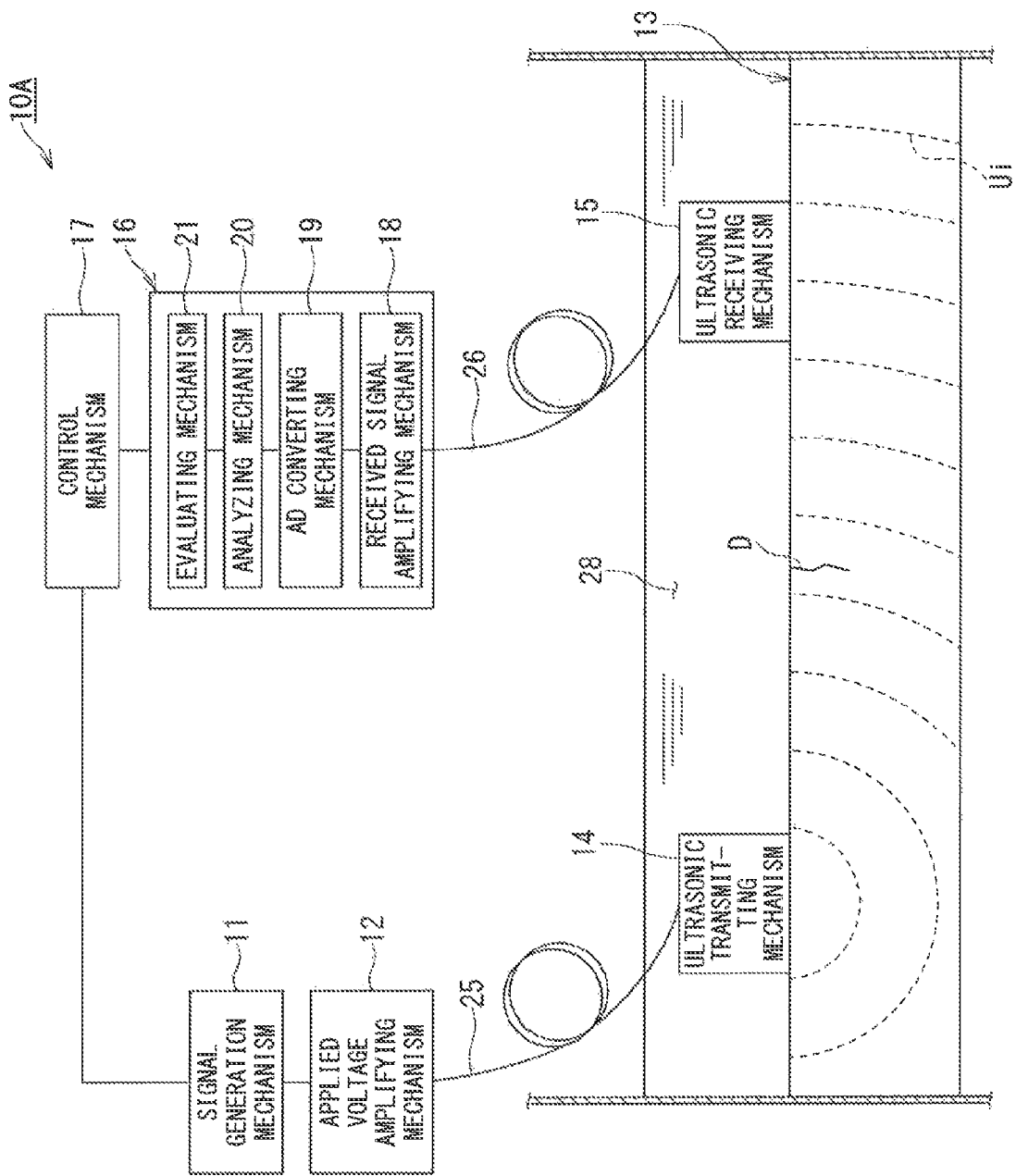
FIG. 12 is a configuration diagram illustrating a second embodiment of the ultrasonic test equipment.

FIG. 12 is a configuration diagram illustrating the second embodiment of the ultrasonic test equipment, in which the same components of an ultrasonic test equipment 10A of the second embodiment and operations as those of the ultrasonic test equipment 10 of the first embodiment are assigned with the same reference numerals, and overlapping description is omitted or simplified herein.

The ultrasonic test equipment 10A of the second embodiment is provided as an example in which the ultrasonic transmitting mechanism 14, the ultrasonic receiving mechanism 15, and the object to be tested 13 out of the ultrasonic test equipment 10 shown in FIG. 1 are installed in water 28 to perform the ultrasonic flaw detection of the defect D in the object to be tested 13.

Examples of the water include pure water, municipal water, industrial water, seawater, and any other liquids having similar electrochemical properties. The ultrasonic transmitting mechanism 14, the ultrasonic receiving mechanism 15, and the cables 25 and 26 connecting the mechanisms have water-proof structures.

As for the water-proof structures, the cables 25 and 26 may be coated with a water-proof material, and the ultrasonic transmitting mechanism 14 and the ultrasonic receiving mechanism 15 may be hermetically sealed in a case in a watertight manner. The ultrasonic transmitting mechanism 14 and the ultrasonic receiving mechanism 15 may be retained in a liquid-tight state by filling a connection section with the cables 25 and 26 with resin or by covering the entire ultrasonic transmitting mechanism 14 and the entire ultrasonic receiving mechanism 15. In any case, the voltage applied portion and the cable portion need to be separated from water and retained in an insulated state.

The other components are the same as those of the ultrasonic test equipment 10 shown in FIG. 1.

First Modification

Figure 13:
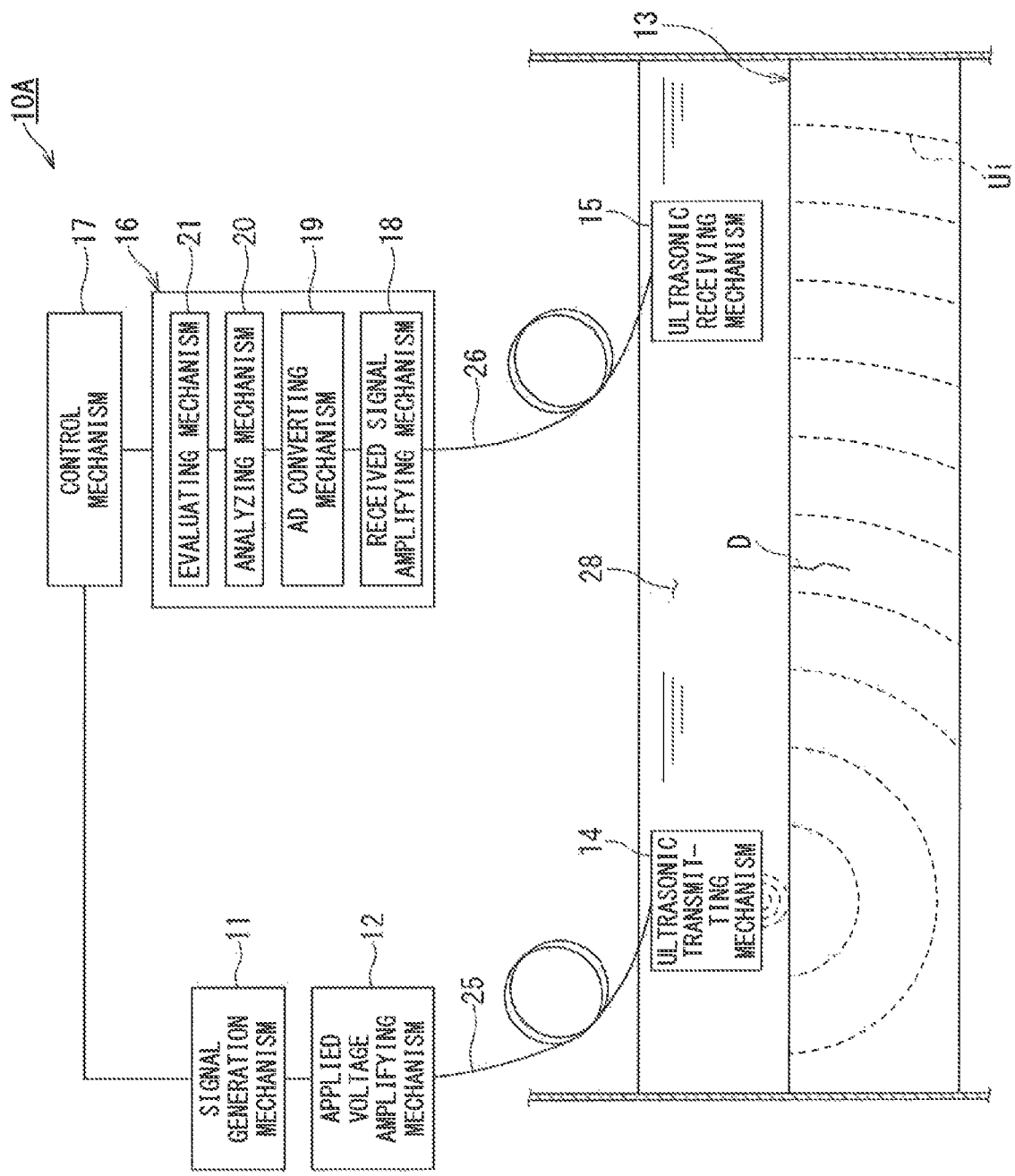
FIG. 13 is a configuration diagram illustrating a first modification of the second embodiment of the ultrasonic test equipment.

FIG. 13 shows the ultrasonic test equipment 10A according to a first modification of the second embodiment.

When the ultrasonic transmitting mechanism 14 and the ultrasonic receiving mechanism 15 are installed in the water 28, the water 28 functions as an acoustic medium. Thus, in the ultrasonic test equipment 10A of the first modification, the ultrasonic transmitting mechanism 14 and the ultrasonic receiving mechanism 15 may be installed with a gap G from the object to be tested 13. The gap G needs to be filled with a generally-used ultrasonic propagation medium, such as water, castor oil, and glycerin paste, or a medium having an equivalent or similar acoustic property.

Second Modification

Figure 14:
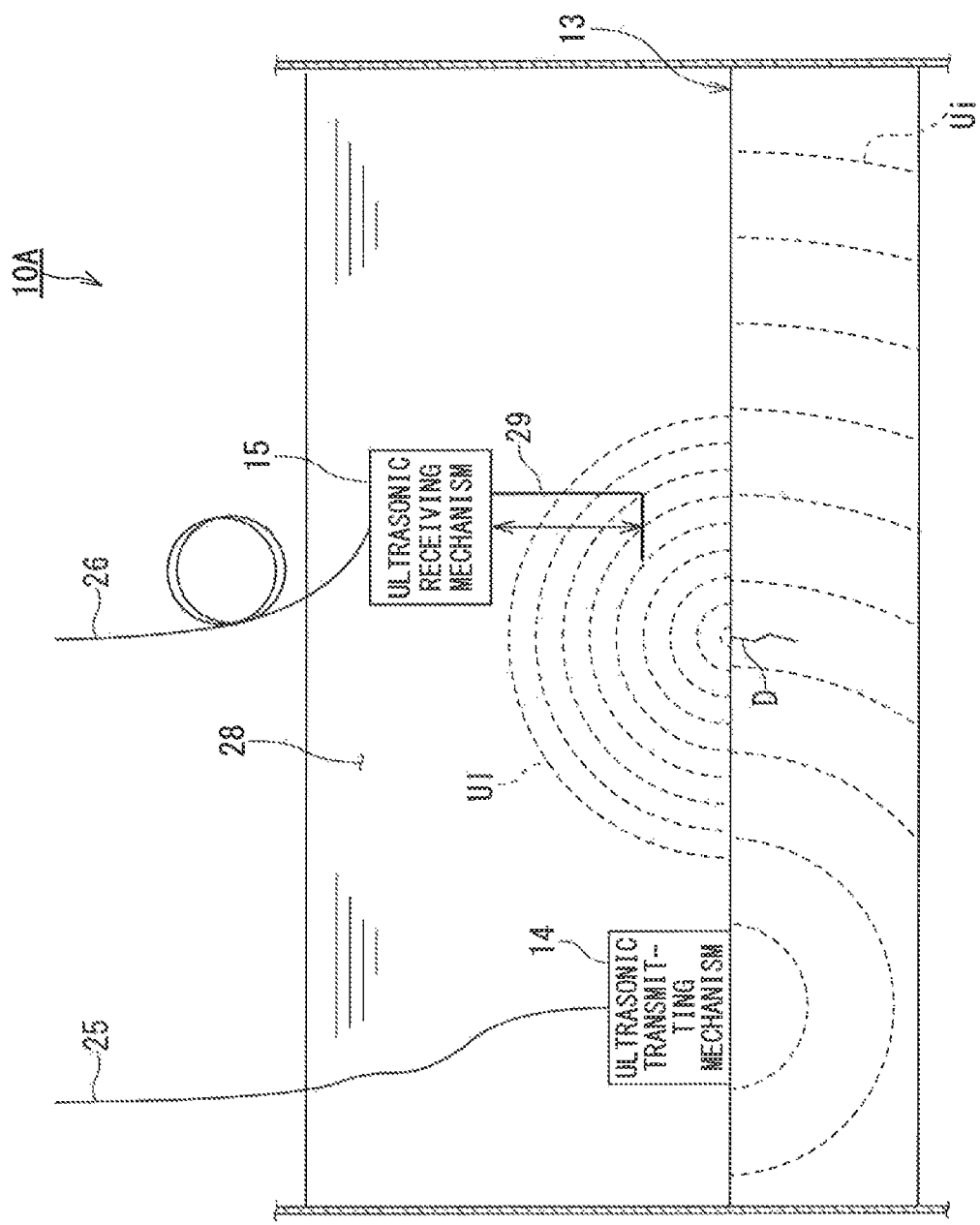
FIG. 14 is a configuration diagram illustrating a second modification of the second embodiment of the ultrasonic test equipment.

FIG. 14 shows the ultrasonic test equipment 10A according to a second modification of the second embodiment.

In the ultrasonic test equipment 10A of the second modification, the ultrasonic receiving mechanism 15 capable of performing ultrasonic measurement in the water 28 is used. For example, a hydrophone, a laser interferometer, and a vibration meter may be used as the ultrasonic receiving mechanism 15.

When the laser interferometer or the vibration meter is used as the ultrasonic receiving mechanism 15, a laser beam may be cast onto the surface of the object to be tested 13. Alternatively, a reflector 29 may be separately arranged in the water 28 so as to observe a change in vibrations leaking into the water 28 from the defect D. The hydrophone may be used to observe the leaking portion of the vibrations leaking into the water.

Operation and Effect of Second Embodiment

In the ultrasonic test equipment 10A of the second embodiment, since the ultrasonic transmitting mechanism 14 and the object to be tested 13 exist in the water 28, the water 28 functions as the acoustic medium (coupling). Thus, even when the ultrasonic transmitting mechanism 14 is not in close contact with the object to be tested 13, the ultrasonic wave Ui can propagate through the object to be tested 13.

When the defect D exists in the object to be tested 13, the nonlinear ultrasonic component generated only from the defect portion leaks into the water 28. Thus, a response from the defect D can be detected in the received ultrasonic wave in the ultrasonic receiving mechanism 15.

At this point, the hydrophone capable of detecting a broad band can be used as the ultrasonic receiving mechanism 15. The laser interferometer can also detect a response in a broad band.

The ultrasonic information of the received ultrasonic wave Ur can be obtained by directly casting a laser beam onto the surface of the object to be tested 13 from the ultrasonic receiving mechanism 15, and measuring the vibrations on the surface of the object 13. However, the reflector 29 may be installed separately from the ultrasonic receiving mechanism 15 as shown in FIG. 14 to observe the reflection.

An optical path change by an elastic wave leaking into the water from the defect D of the object 13 can be thereby measured with stable sensitivity.

The actions and operations of the ultrasonic transmitting mechanism 14, the applied voltage amplifying mechanism 12, and the received signal amplifying mechanism 18, the AD converting mechanism 19, the analyzing mechanism 20 and the evaluating mechanism 21 of the signal processor 16 by the control mechanism 17 are the same as those of the ultrasonic test equipment 10 described in the first embodiment.

Third Embodiment

Figure 15:
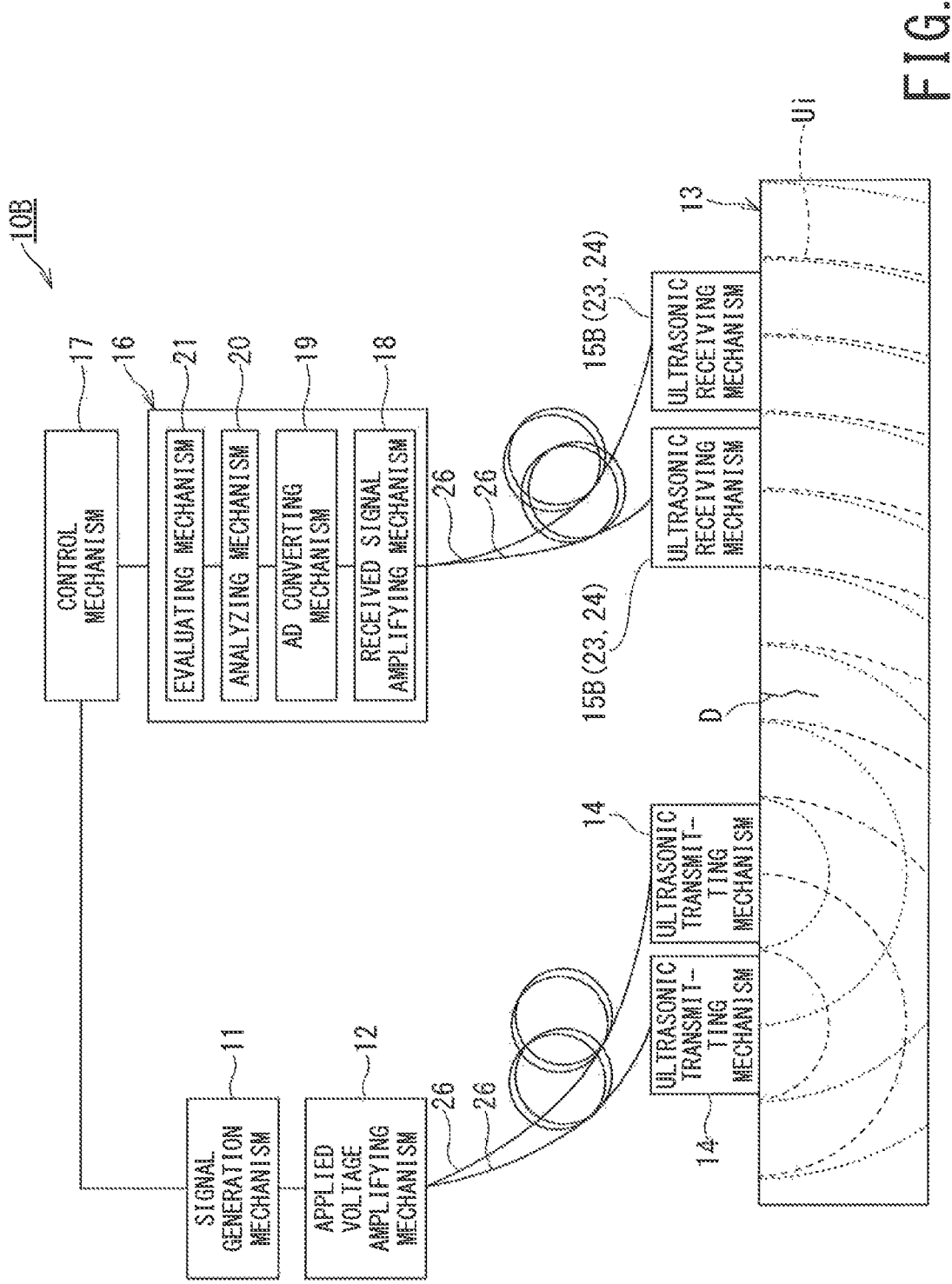
FIG. 15 is a configuration diagram illustrating a third embodiment of the ultrasonic test equipment.
Figure 16:
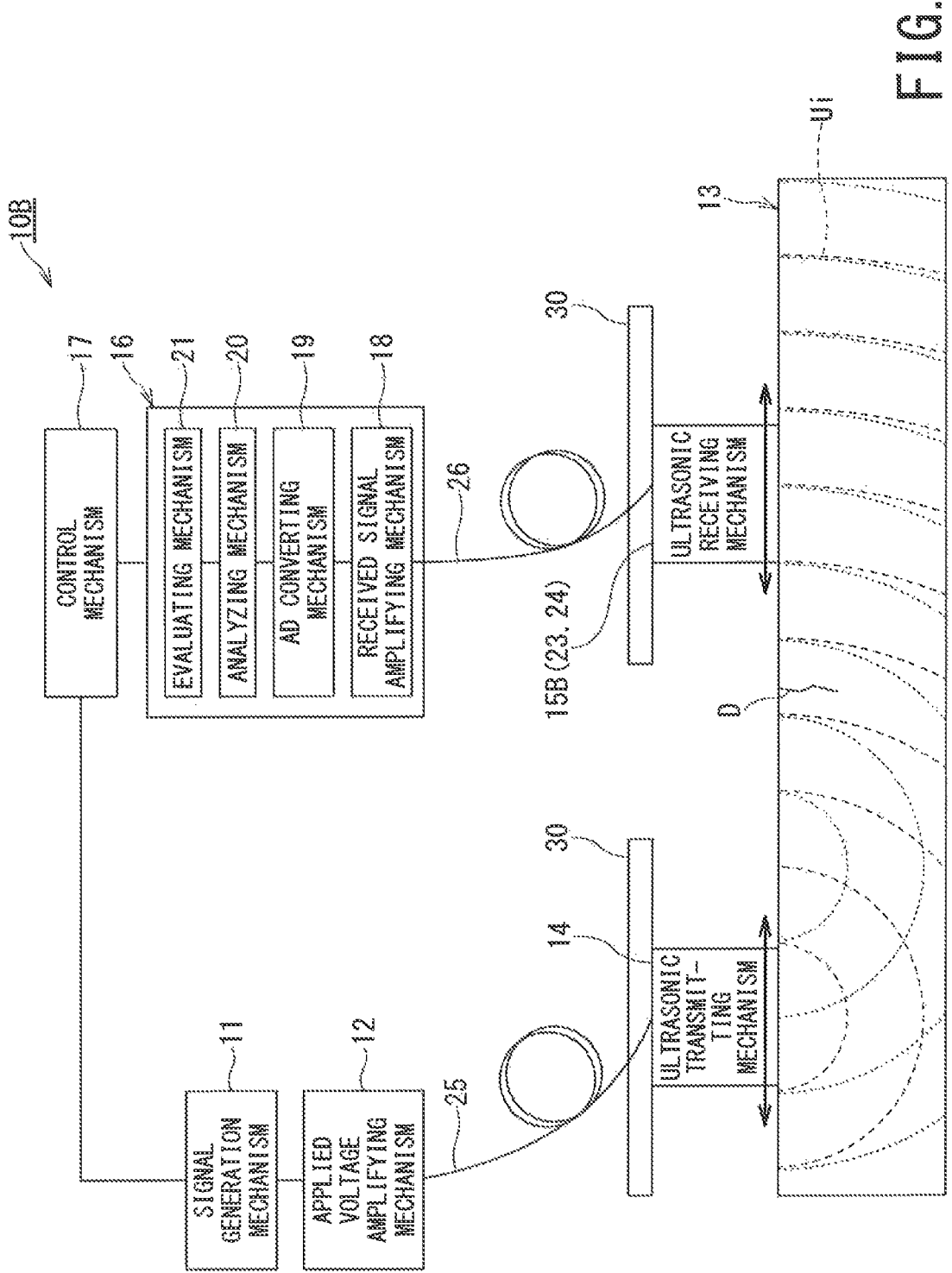
FIG. 16 is a configuration diagram illustrating a first modification of the third embodiment of the ultrasonic test equipment.

FIGS. 15 and 16 are configuration diagrams illustrating a third embodiment of the present invention.

In an ultrasonic test equipment 10B of the third embodiment, at least one of the ultrasonic transmitting mechanism 14 and the ultrasonic receiving mechanism 15B is installed at a plurality of positions as shown in the configuration diagram of FIG. 15. Since the other components of the ultrasonic test equipment 10B are the same as those of the ultrasonic test equipments 10 and 10A described in the first and second embodiments, the same components are assigned with the same reference numerals, and overlapping description is omitted or simplified herein.

In the ultrasonic test equipment 10B shown in FIG. 15, a plurality (e.g., two) of ultrasonic transmitting mechanisms 14 and a plurality (e.g., two) of ultrasonic receiving mechanisms 15B are installed.

First Modification

In a first modification of the third embodiment shown in FIG. 16, a scanning mechanism 30 is provided in each of the ultrasonic transmitting mechanism 14 and the ultrasonic receiving mechanism 15 of the ultrasonic test equipment 10B. Since the other components are the same as those of the ultrasonic test equipment 10 described in the first embodiment, the same components are assigned with the same reference numerals, and overlapping description will be omitted.

In the ultrasonic test equipment 10B shown in FIG. 16, the ultrasonic transmitting mechanism 14 and the ultrasonic receiving mechanism 15 are in close contact with the object to be tested 13. This configuration can be applied to the configuration in water or the ultrasonic test equipment 10A of the second embodiment using the laser-ultrasonics.

In the ultrasonic test equipment 10B of the third embodiment, a plurality of signals are obtained from at least one of the plurality of ultrasonic transmitting mechanisms 14 and the plurality of ultrasonic receiving mechanisms 15 as shown in FIG. 15. The analyzing mechanism 20 identifies a signal generation position of the defect D from the plurality of signals by using a method such as correlation processing and signal processing of temporal information like a time-of-flight method, Operation and Effect of Third Embodiment In the ultrasonic test equipment 10B described in the third embodiment, the plurality of ultrasonic transmitting mechanisms 14 and the plurality of ultrasonic receiving mechanisms 15 are provided as shown in FIG. 15. Thus, the received ultrasonic wave Ur signal is obtained at a plurality of points. The signal is also obtained at a plurality of points by moving the ultrasonic transmitting mechanism 14 and the ultrasonic receiving mechanism 15 respectively by using the scanning mechanisms 30 as shown in FIG. 16.

The correlation processing is then performed by using the received waveform obtained at a plurality of points in the test, and a received waveform (hereunder, referred to as reference waveform) recorded on a recording device in advance and obtained when there is no defect in the object to be tested 13, that is, obtained from an object to be tested with no defect.

The reference waveform is prepared by, for example, acquiring the received waveform when a crack has not been generated in the object to be tested 13 (e.g., immediately after production or soon after the product starts to be used), performing flaw detection on a mock-up of the object to be tested 13, or generating the received waveform by a simulation.

A reference ultrasonic signal of an ultrasonic wave directly reaching the ultrasonic receiving mechanism 15 from the ultrasonic transmitting mechanism 14 without passing through the defect is obtained from the reference waveform. The received waveform Ur of an actual test signal includes a defect signal (a defect echo Ud) of an ultrasonic wave reaching the defect D, an ultrasonic signal of an ultrasonic wave directly reaching the received position from the ultrasonic transmitting mechanism 14 without passing through the defect D, and an ultrasonic signal of an ultrasonic wave reflected from an non-defective end surface such as a corner of the object 13. When the correlation processing is performed, the ultrasonic signals other than the defect signal exhibit a strong correlation with the reference ultrasonic signal obtained from the reference waveform.

The defect signal does not exhibit a correlation since the defect signal has a nonlinear ultrasonic frequency component as described above. Therefore, only the characteristic ultrasonic signal derived from the defect can be extracted by performing a removal process of removing the signals with the reference waveform exhibiting a correlation equal to or more than a predetermined value from the digital ultrasonic waveform. By removing the ultrasonic signals from the digital received ultrasonic waveform obtained by the actual test, the characteristic ultrasonic signal from the defect can be extracted.

The digital received ultrasonic waveform including the characteristic ultrasonic signal from the defect D is obtained at a plurality of points. By using the plurality of digital received ultrasonic waveforms, the analyzing mechanism 20 performs imaging using a time domain such as a synthetic aperture method, or a position identification process such as a time-of-flight method. The analyzing mechanism 20 can thereby identify the position of the defect D based on the characteristic ultrasonic signal of the digital ultrasonic waveform from the defect (after removing the signals exhibiting the correlation equal to or more than a predetermined value). Accordingly, the ultrasonic test equipment 10B can identify the position of the defect D in the object to be tested 13.

Fourth Embodiment

Figure 17B:
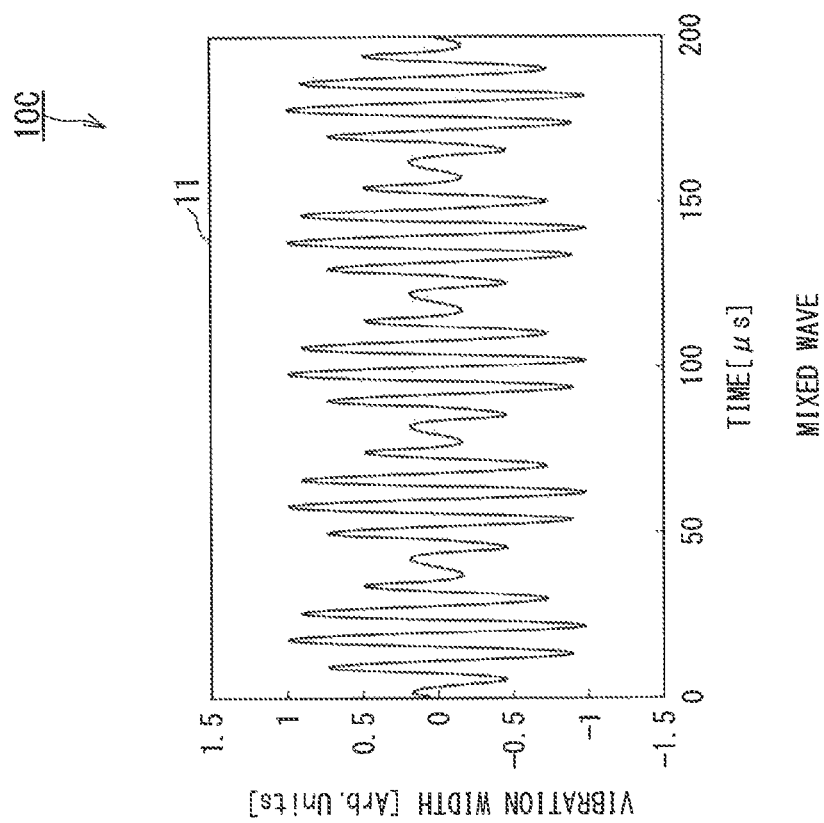
FIGS. 17A and 17B shows a fourth embodiment of the ultrasonic test equipment, in which FIG.
Figure 17A:
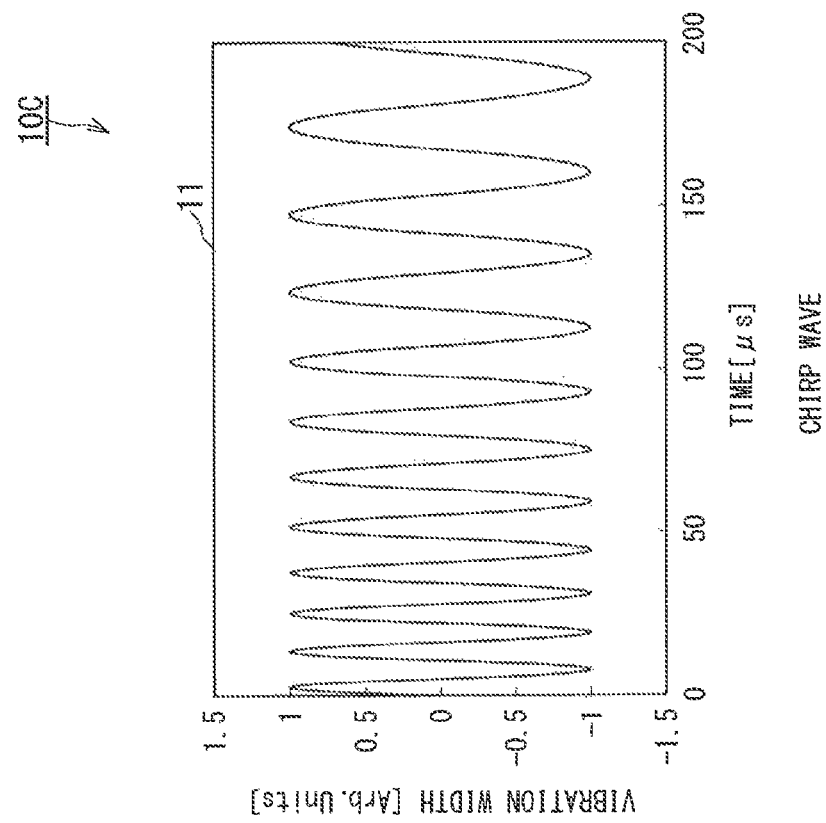
Figure 18:
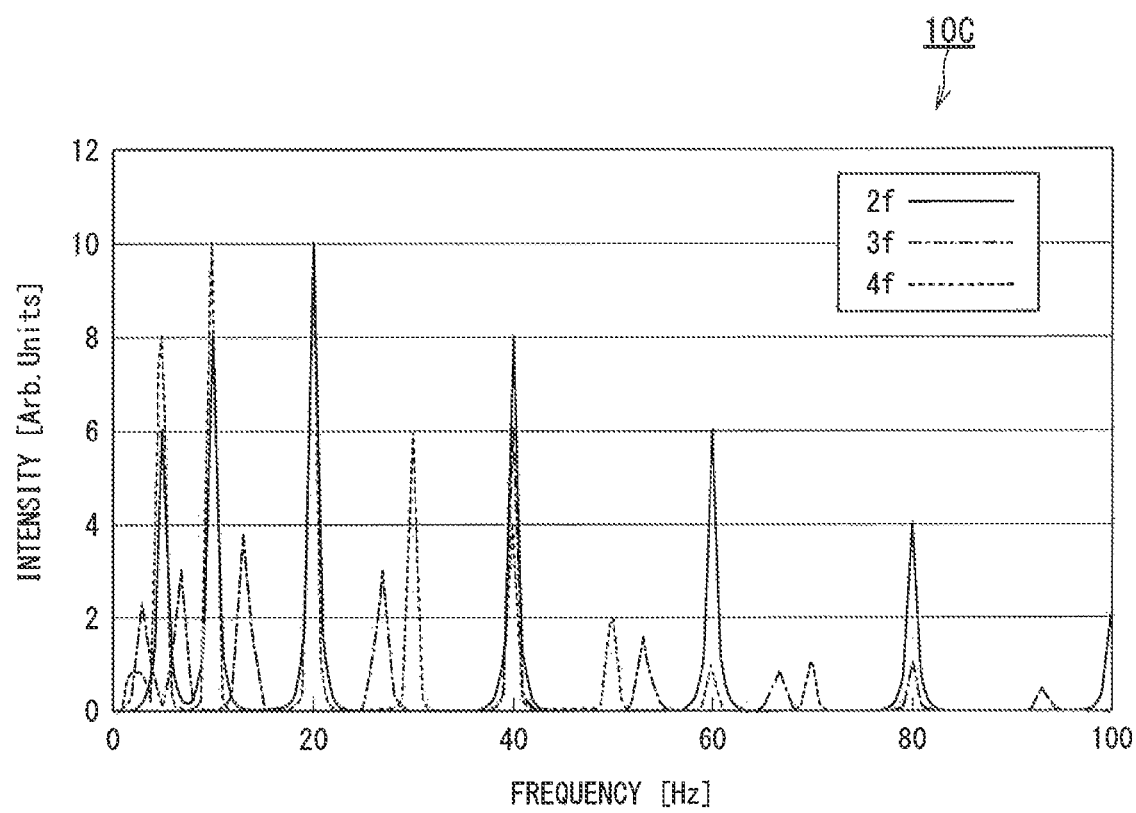
FIG. 18 is an explanatory view illustrating a relationship between a generation efficiency of a nonlinear component from a defect portion in an object to be tested and a frequency.

FIGS. 17 and 18 are views for explaining a fourth embodiment of the present invention.

Since an entire configuration of an ultrasonic test equipment 10C of the fourth embodiment is not different from those of the ultrasonic test equipments 10 to 10B described in the first to third embodiments, the same components are assigned with the same reference numerals, and overlapping description is omitted or simplified herein.

In the ultrasonic test equipment 10C of the fourth embodiment, the signal generating mechanism 11 includes a mechanism for sweeping the transmitted waveform into a chirp wave or the like as shown in FIG. 17A, and a mechanism for mixing a plurality of frequency components of the transmitted waveform as shown in FIG. 17B.

As a method of sweeping the transmitted waveform generated in the signal generating mechanism 11, the frequency may be continuously changed like a chirp wave, or randomly changed like an M-sequence wave. A mixed wave may be composed of multiplied sinusoidal waves having different frequencies.

The signal generating mechanism 11 has a function to sweep the frequency of the voltage waveform that is the transmitted waveform. The analyzing mechanism 20 analyzes the tendency of the generation efficiency of the nonlinear ultrasonic component in response to the frequency change in the digital ultrasonic waveform obtained from the ultrasonic receiving mechanism 15 through the AD converting mechanism 19. The evaluating mechanism 21 has a function to acquire at least one of the physical quantities of the length, depth, opening width and opening stress of the defect in the object to be tested 13 by matching the frequency information of the analyzed digital ultrasonic waveform with the known defect data information in the defect information database.

The signal generating mechanism 11 also has a function to generate the voltage waveform having a plurality of mixed frequencies. The analyzing mechanism 20 analyzes the tendency of the generation efficiency of the nonlinear ultrasonic component in response to the frequency change in the digital ultrasonic waveform obtained from the ultrasonic receiving mechanism 15 through the AD converting mechanism 19. The evaluating mechanism 21 has a function to acquire at least one of the physical quantities of the length, depth, opening width and opening stress of the defect in the object to be tested 13 by matching the frequency information of the analyzed digital ultrasonic waveform with the known defect data information in the defect information database.

Operation and Effect of Fourth Embodiment

The ultrasonic test equipment 10C of the fourth embodiment can also observe the generation efficiency in the nonlinear phenomenon at a specific frequency or a combination of specific frequencies by changing the frequency of the transmitted waveform generated in the signal generating mechanism 11. The generation efficiency of the nonlinear component from the defect D of the object to be tested 13 is determined by the incident frequency fi into a defect profile such as a defect shape. Accordingly, the generation efficiency can be analyzed as shown in FIG. 18 in which the vertical axis represents a scale intensity and the horizontal axis represents a frequency. The accuracy of the defect sizing of the defect D in the object to be tested 13 is further improved.

Fifth Embodiment

Figure 19:
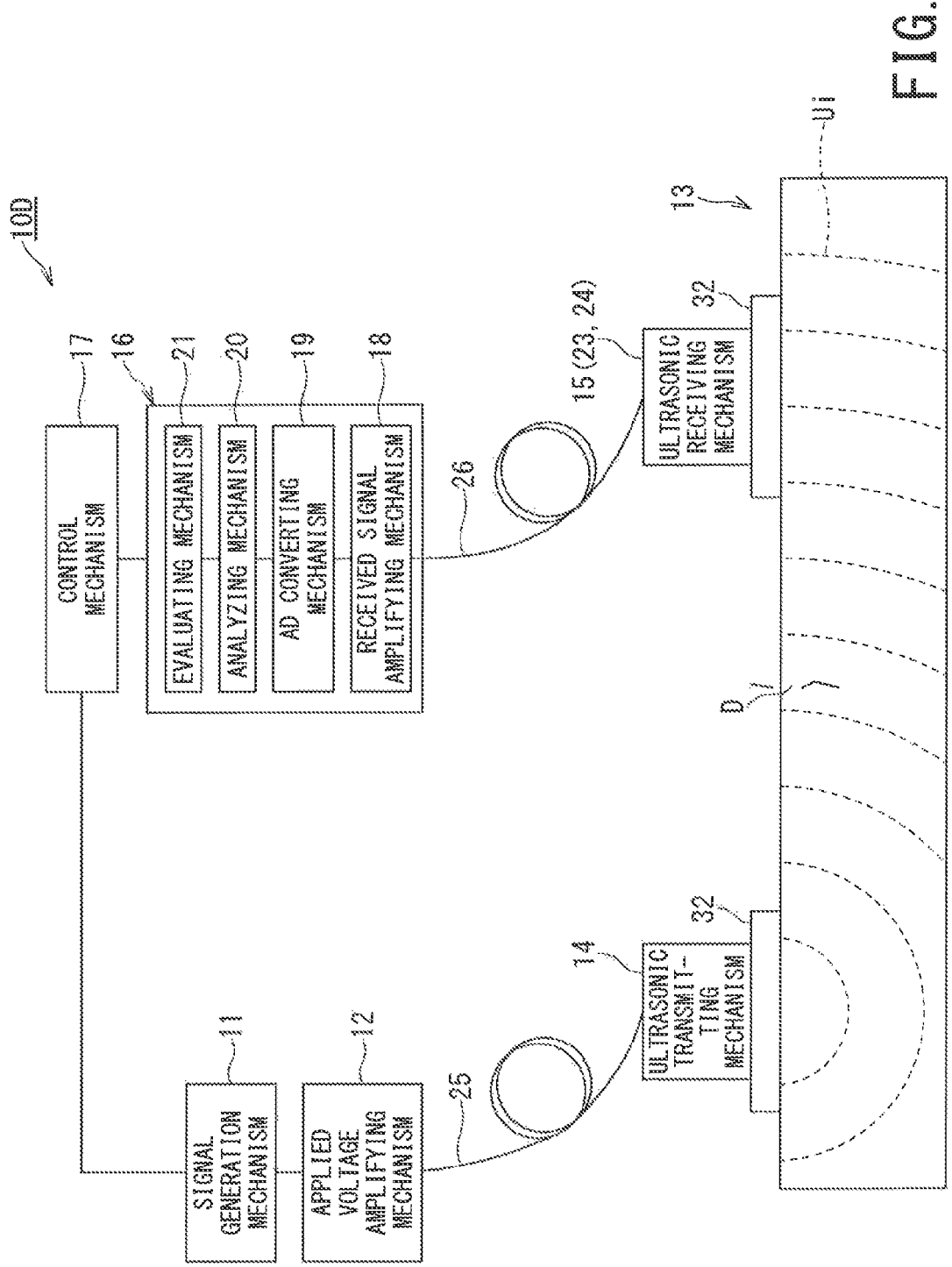
FIG. 19 is a configuration diagram illustrating a fifth embodiment of the ultrasonic test equipment.

FIG. 19 is a configuration diagram illustrating a fifth embodiment of the present invention.

In an ultrasonic test equipment 101) of the fifth embodiment, an acoustic impedance matching layer (coupling layer) 32 that improves ultrasonic propagation efficiency is provided between at least one of the ultrasonic transmitting mechanism 14 and the ultrasonic receiving mechanism 15, and the object to be tested 13. Since the other components and operations are the same as those of the ultrasonic test equipments 10 and 10A to 10C described in the first to fourth embodiments, the same components are assigned with the same reference numerals, and overlapping description is omitted or simplified herein.

In the ultrasonic test equipment 1013 shown in FIG. 19, the coupling layer 32 is provided between the ultrasonic transmitting mechanism 14 and the object to be tested 13 and between the ultrasonic receiving mechanism 15 and the object to be tested 13. The coupling layer 32 is made of a polymer material called shoe used for the ultrasonic testing technique, or a coupling member such as water and gel. The coupling layer 32 is provided so as to couple the ultrasonic transmitting mechanism 14 and the ultrasonic receiving mechanism 15 to the object 13 in acoustic impedance.

The coupling layer 32 prevents a layer of air or the like from being formed between the ultrasonic transmitting mechanism 14 or the ultrasonic receiving mechanism 15 and the object to be tested 13, thereby blocking the ultrasonic propagation.

Operation and Effect of Fifth Embodiment

In the ultrasonic test equipment 10D of the fifth embodiment, the ultrasonic wave can be more effectively transmitted from the ultrasonic transmitting mechanism 14 to the object to be tested 13 and received by the ultrasonic receiving mechanism 15 from the object 13 by acoustically coupling the ultrasonic transmitting mechanism 14 and the ultrasonic receiving mechanism 15 to the object 13 by the coupling layer 32 interposed therebetween.

Particularly, when the ultrasonic test equipment 10D of the fifth embodiment is used to perform the ultrasonic flaw detection of the object to be tested 13 in the air, it is necessary to bring the ultrasonic transmitting mechanism 14 into close contact with the object 13. Since the coupling layer 32 is interposed between the ultrasonic transmitting mechanism 14 and the object to be tested 13, the coupling layer 32 fills a space in the air. Accordingly, an acoustic matching property is obtained even when the ultrasonic transmitting mechanism 14 is not in close contact with the object to be tested 13.

Even when the surface of the object 13 has a complicated shape such as a curved surface, or the surface is coarse or deformed, the low-frequency and large-amplitude incident ultrasonic wave Ui from the ultrasonic transmitting mechanism 14 can be caused to smoothly and stably enter the object to be tested 13 by interposing the coupling layer 32 between the ultrasonic transmitting mechanism 14 and the object to be tested 13.

The received ultrasonic wave Ur can be also smoothly and stably received by the ultrasonic receiving mechanism 15 by interposing the coupling layer 32 between the object 13 and the ultrasonic receiving mechanism 15.

Sixth Embodiment

Figure 20:
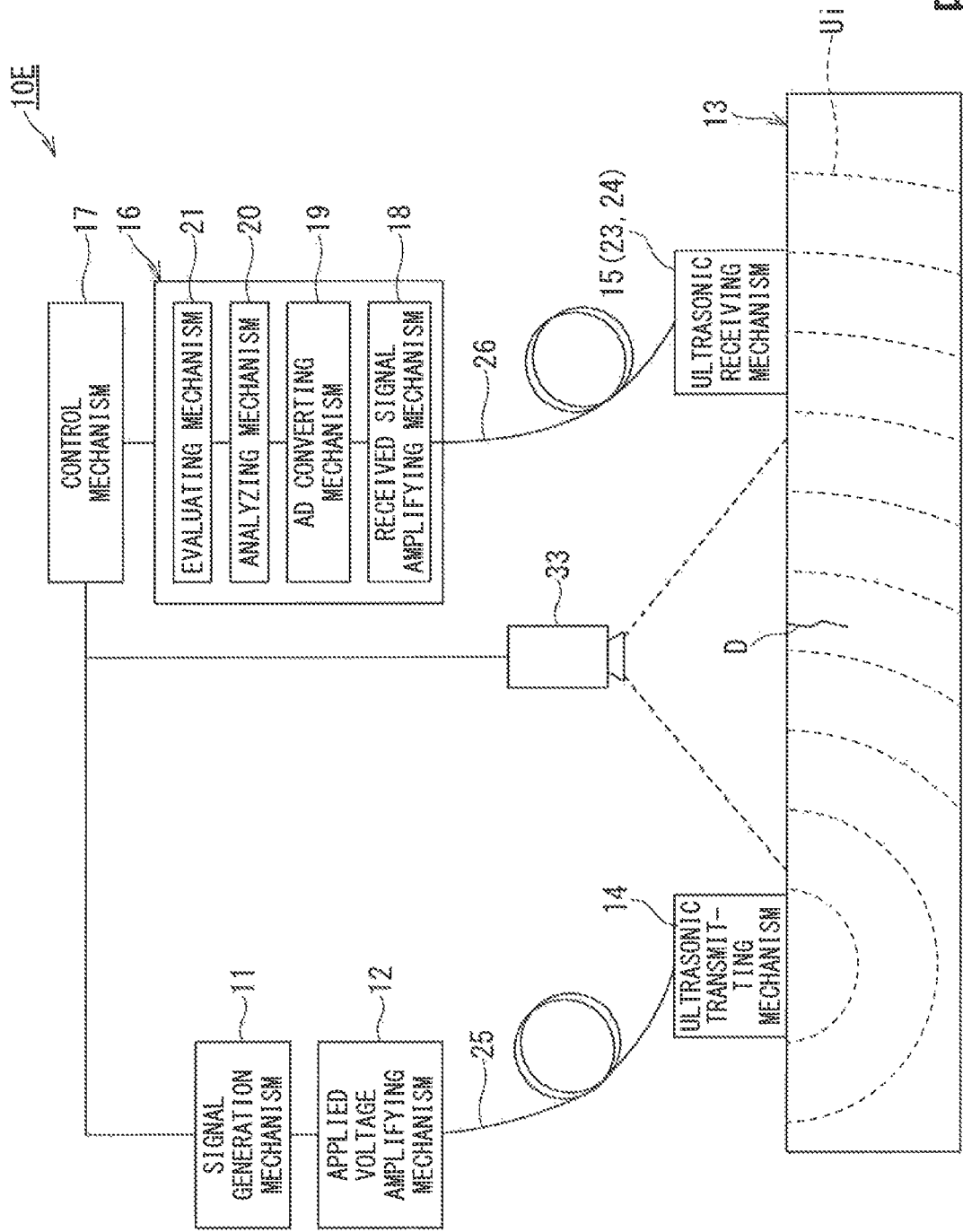
FIG. 20 is a configuration diagram illustrating a sixth embodiment of the ultrasonic test equipment.
Figure 21:
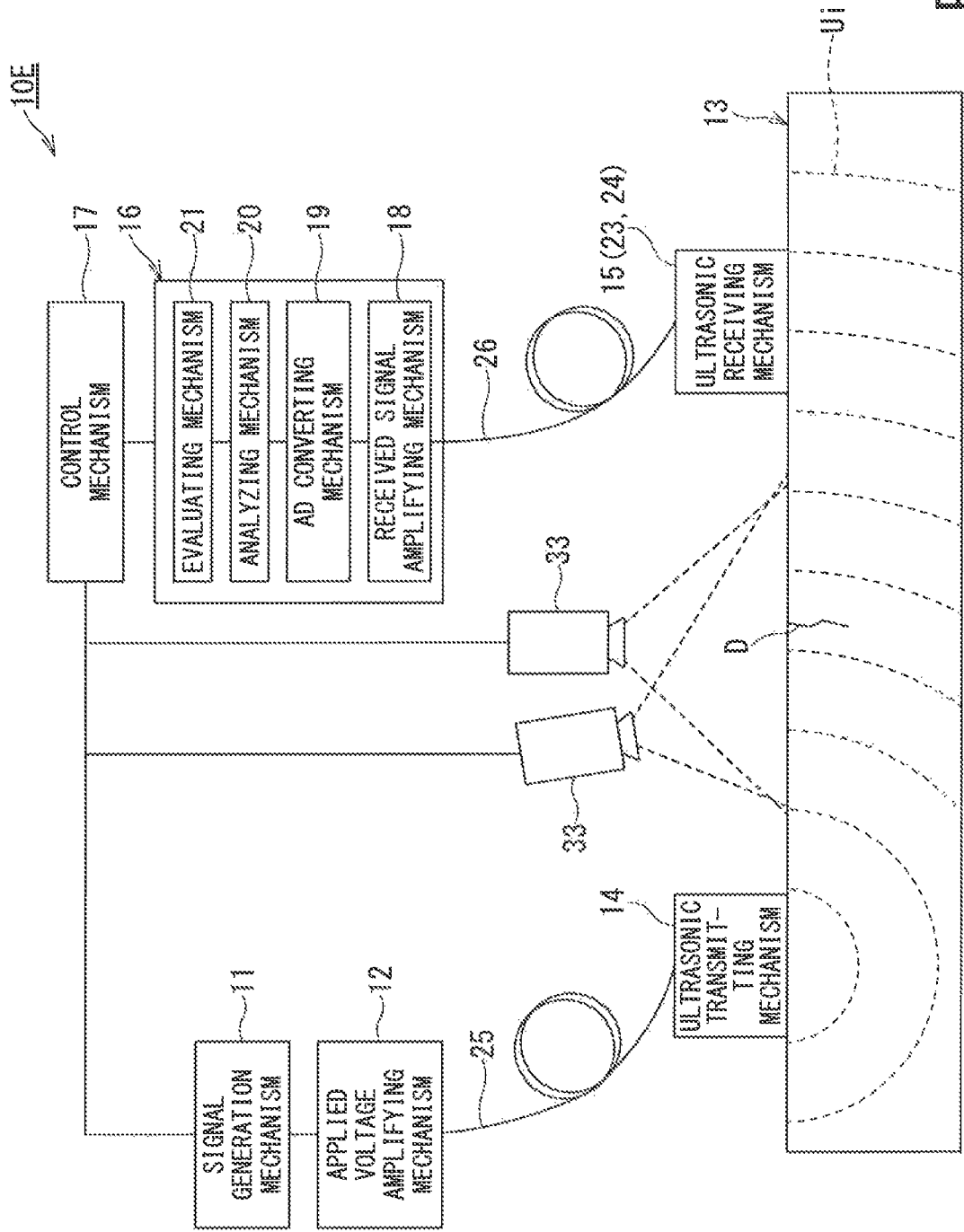
FIG. 21 is a configuration diagram illustrating a first modification of the sixth embodiment of the ultrasonic test equipment.
Figure 22:
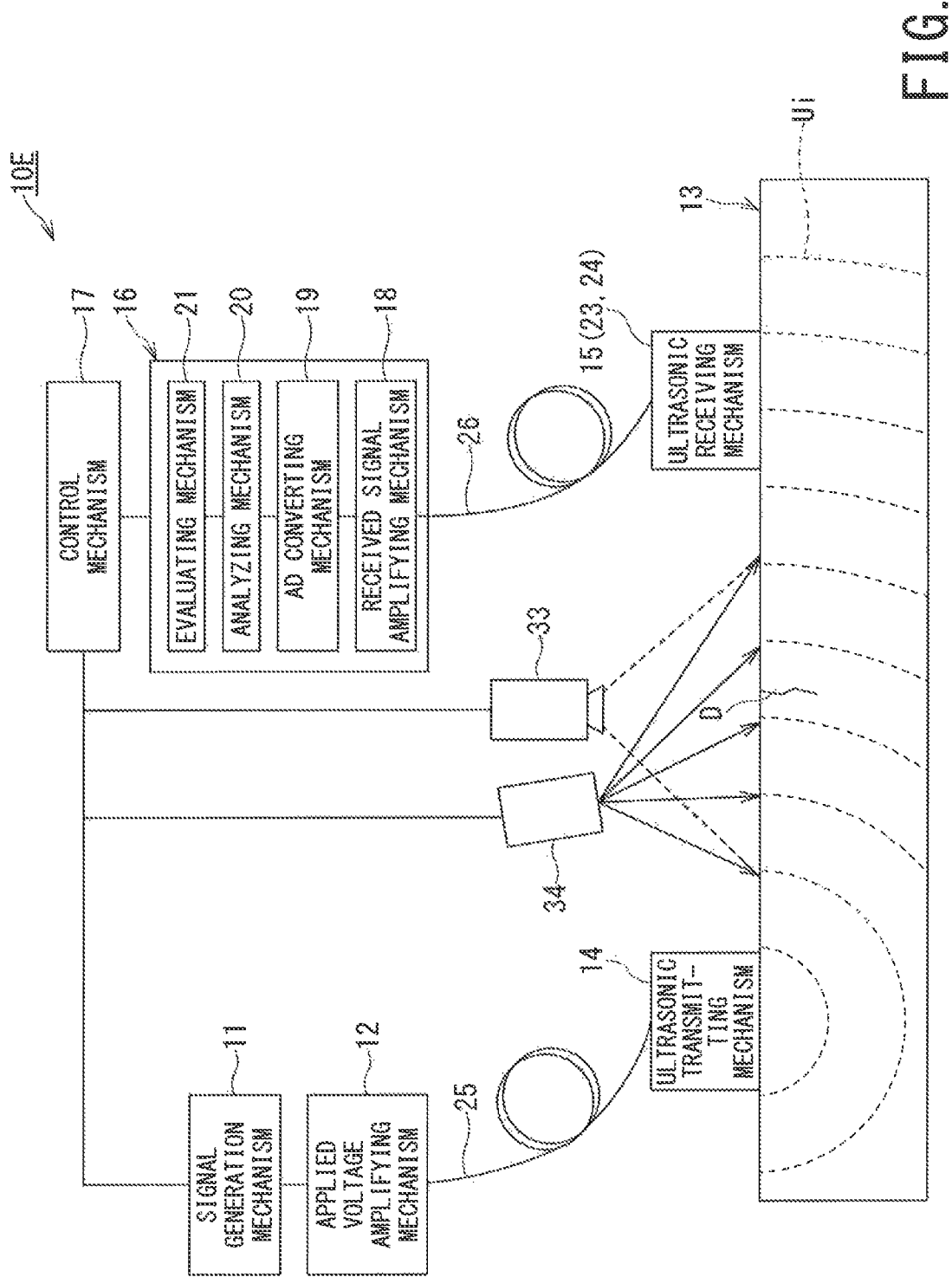
FIG. 22 is a configuration diagram illustrating a second modification of the sixth embodiment of the ultrasonic test equipment.

FIGS. 20 to 22 are configuration diagrams illustrating a sixth embodiment of the present invention.

In an ultrasonic test equipment 10E of the sixth embodiment, a remote viewing mechanism 33 is provided in the ultrasonic test equipments 10 and 10A to 10D described in the first to fifth embodiments. Since the other components are the same as those of the ultrasonic test equipments 10 and 10A to 10D described in the first to fifth embodiments, the same components are assigned with the same reference numerals, and overlapping description is omitted or simplified herein.

In the ultrasonic test equipment 10E shown in FIG. 20, the monocular remote viewing mechanism 33 capable of recording optical information of the surface of the object to be tested 13 is provided above the object 13. The remote viewing mechanism 33 is composed of a general optical camera, a small camera such as an endoscope, or the like. The optical information viewed by the remote viewing mechanism 33 can be created by using lights with various wavelengths, Not only a visible light of 380 to 780 nm, but also infrared rays, ultraviolet rays, and X rays may be used.

The ultrasonic test equipment 10E also has a function to specifically identify the position of the defect D in the object to be tested 13 by superimposing the information such as the position of the defect D in the object 13 obtained by the analyzing mechanism 20 of the signal processor 16 on an image obtained by the remote viewing mechanism 33.

Although FIG. 20 shows the example in which the remote viewing mechanism 33 is independently installed in the ultrasonic test equipment 10E, the remote viewing mechanism 33 may be attached to the ultrasonic transmitting mechanism 14 or the ultrasonic receiving mechanism 15.

First Modification

FIG. 21 is a configuration diagram illustrating a first modification of the sixth embodiment of the ultrasonic test equipment 10E.

While the ultrasonic test equipment 10E shown in FIG. 20 includes the monocular remote viewing mechanism 33, the ultrasonic test equipment 10E of the first modification includes a plurality of remote viewing mechanisms 33 and 33, thereby constituting an algorithm of a stereoscopic binocular remote viewing mechanism 33. The other components are the same as those of the ultrasonic test equipment 10E described in the sixth embodiment, Second Modification FIG. 22 is a configuration diagram illustrating a second modification of the sixth embodiment of the ultrasonic test equipment 10E.

In the ultrasonic test equipment 10E of the second modification, the remote viewing mechanism 33 is used in combination with a pattern laser 34. The other components are the same as those of the ultrasonic test equipment 10E described in the sixth embodiment, Operation and Effect of Sixth Embodiment In the ultrasonic test equipment 10E described in the sixth embodiment, the detection result of the defect D in the object to be tested 13 analyzed by the analyzing mechanism 20 of the signal processor 16 is superimposed on the remote visual image of the object 13 obtained in the remote viewing mechanism 33, and displayed on a display device, not shown. Accordingly, the quantitative flaw detection result such as the position, length, and depth of the defect D in the object 13 can be more specifically evaluated and detected.

The surface shape of the object to be tested 13 is measured by the remote viewing mechanism 33 of the ultrasonic test equipment 10E in a stereoscopic manner using the plurality of cameras or in combination with the pattern laser for effecting shape measurement. Accordingly, the accuracy of identifying the position of the defect D can be improved.

Seventh Embodiment

Figure 23:
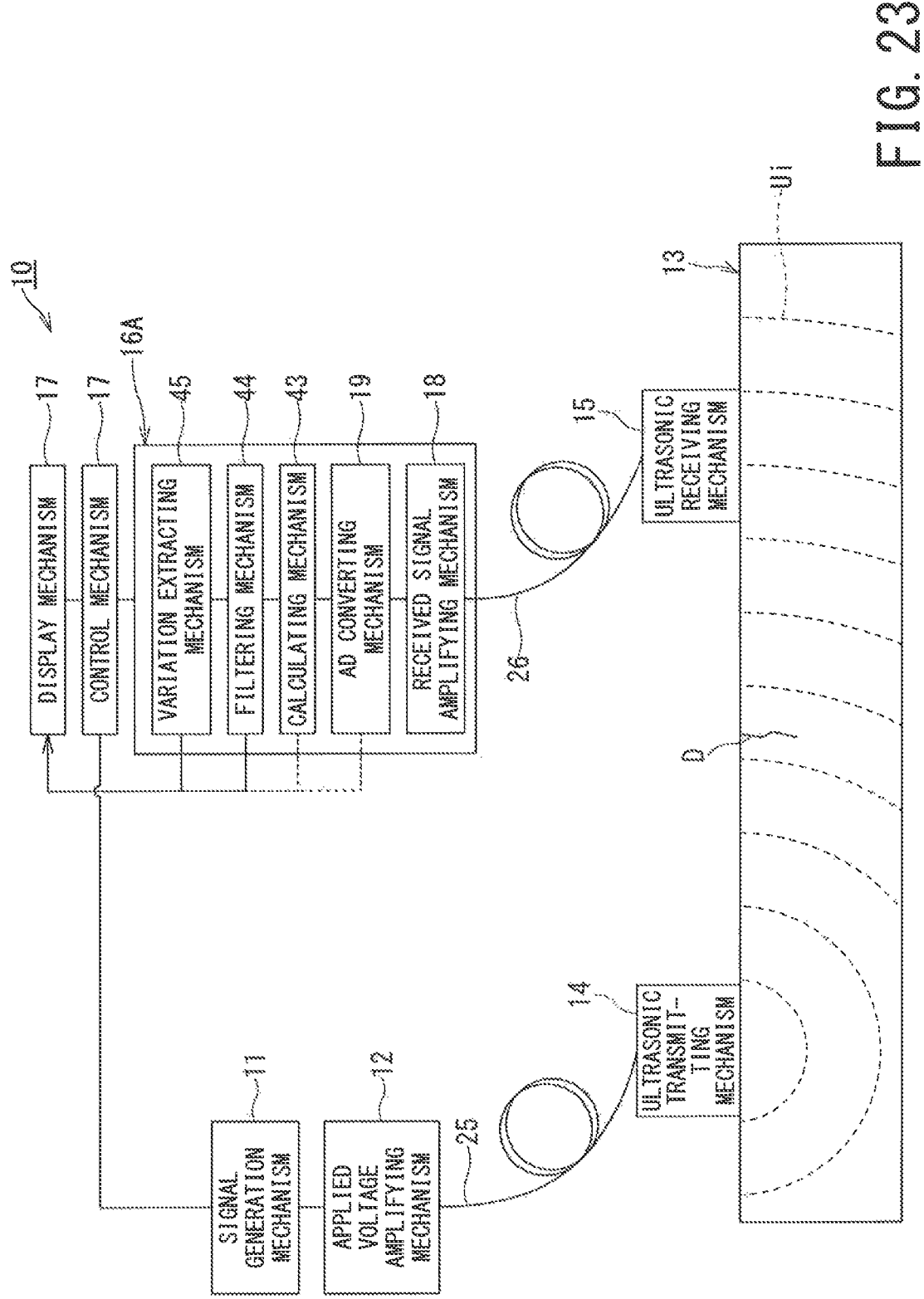
FIG. 23 is a configuration diagram illustrating a seventh embodiment of the ultrasonic test equipment.

FIG. 23 shows a seventh embodiment of the ultrasonic test equipment and represents a configuration example of the ultrasonic test equipment which can nondestructively and extensively detect the defect (the volume defect) in the surface and the inner portion of the object to be tested 13, and which can also acquire the physical quantities of the defect information such as the length and depth of the defect. Further, it is to be noted that the same components and operations as those of the ultrasonic test equipment described in the first embodiment are assigned with the same reference numerals, and overlapping description is omitted or simplified herein.

An ultrasonic test equipment 10F of the seventh embodiment includes a signal processor 16A instead of the signal processor 16 of the first embodiment. The ultrasonic test equipment 10F further includes a display mechanism 40 that displays a portion or all of the ultrasonic waveform or calculation data (physical information) processed in the signal processor 16A.

The signal processor 16A includes the received signal amplifying mechanism 18, the AD converting mechanism 19, a calculating mechanism 43, a filtering mechanism 44, and a variation extracting mechanism 45.

The calculating mechanism 43 performs an inverse problem calculation (analysis) by obtaining a harmonic component or a subharmonic component from the digital ultrasonic (waveform) signal by processing such as a fast Fourier transform (FFT), performing processing such as an inverse fast Fourier transform (IFFT) on a (scattering source) spatial intensity distribution of the obtained harmonic component or the like, and thereby identifying the defect position.

The filtering mechanism 44 calculates the physical quantity of the defect position based on the (scattering source) spatial intensity distribution filtered by any frequency component (a frequency of an order whose harmonic or subharmonic component has a large scale intensity).

The variation extracting mechanism 45 extracts an intensity variation of the nonlinear ultrasonic component.

The signal generating mechanism 11 includes a modulating mechanism that temporally changes the amplitude of the analog voltage signal.

The calculating mechanism 43 of the signal processor 16A has a function to calculate the spatial intensity distribution by obtaining the harmonic or subharmonic component from an echo of the received ultrasonic signal Ur that is the digital ultrasonic waveform sent from the AD converting mechanism 19 by the fast Fourier transform (FFT), and performing the inverse problem analysis on the harmonic component or the like by the inverse fast Fourier transform (IFFT), to obtain which (spatial) position in the object 13 an echo of a reflected ultrasonic wave comes from. Examples of the calculating method include a basic time-of-flight method and an analysis method such as correlation processing and synthetic aperture processing using a plurality of received ultrasonic signals Ur. Of course, a signal processing method other than those described above may be employed.

The filtering mechanism 44 of the signal processor 16A may have an analog or digital configuration. In the case of the digital configuration, the filtering mechanism 44 may be provided as a signal processing circuit, or software incorporated in the control mechanism 17 or the like. Examples of a filter used in the filtering mechanism 44 include high-pass, low-pass, band-pass, band-elimination filters. A transfer function of a Butterworth filter, a Bessel filter, a Chebyshev filter, an elliptic Chebyshev filter, a comb filter, and an FFT-IFFT filter may be used. Of course, a filter other than those described above may be employed.

The filtering mechanism 44 identifies the spatial position or the like of the defect D by filtering the harmonic (subharmonic) component of the spatial intensity distribution of the digital ultrasonic waveform obtained from the calculating mechanism 43 by any frequency component (a frequency component of an order having a large scale intensity), and calculating the spatial intensity distribution of, for example, the second-order harmonics 2fi in FIG. 11A.

The variation extracting mechanism 45 of the signal processor 16A is a mechanism for extracting the nonlinear ultrasonic component obtained from a plurality of measurement points. The variation extracting mechanism 45 can calculate the generation efficiency of the nonlinear ultrasonic component that changes depending on the presence of the defect D.

The display mechanism 40 of the ultrasonic test equipment 10F has a function to display a portion or all of the digital ultrasonic waveform processed in the AD converting mechanism 19, the (scattering source) spatial intensity distribution processed in the calculating mechanism 43, the (scattering source) spatial intensity distribution processed in the filtering mechanism 44, and the intensity variation processed in the variation extracting mechanism 45. The display mechanism 40 can also display the incident ultrasonic frequency or measurement conditions. Output signals from the filtering mechanism 44 and the variation extracting mechanism 45 are basically displayed on the display mechanism 40. Output signals from the AD converting mechanism 19 and the calculating mechanism 43 may be also introduced in and displayed on the display mechanism 40. At least the filtered spatial intensity distribution from the filtering mechanism 44 is displayed on the display mechanism 40. The display mechanism 40 may be a touch panel or the like so as to allow a user to directly input the information from a screen.

Operation of Seventh Embodiment

Next, an operation of the ultrasonic test equipment 10F will be described.

Figure 24:
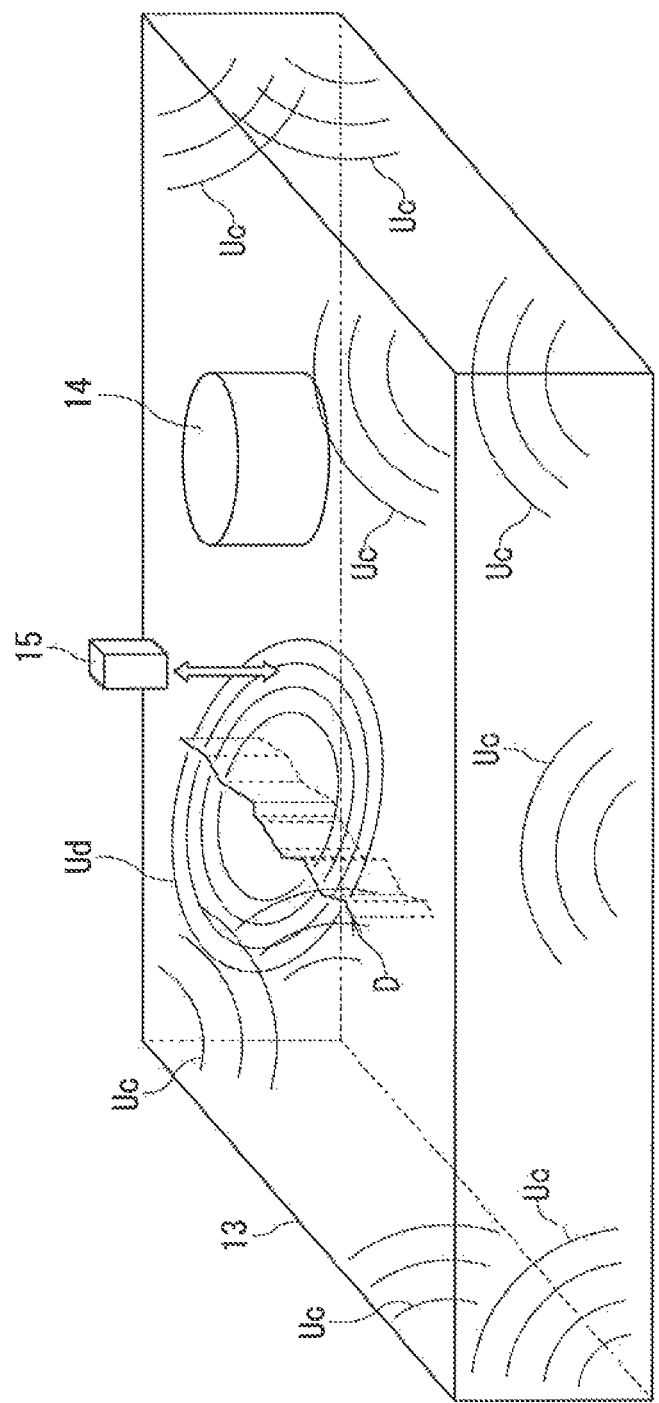
FIG. 24 is an explanatory view of the shape of an object to be tested, and a propagation example of an ultrasonic echo from a defect.

As described above, the large-amplitude incident ultrasonic wave Ui propagates in a wide range of the object to be tested 13. Thus, there may cause a case in which a response is obtained from a position other than the defect D in the object to be tested 13 as shown in FIG. 24. Although some responses are generated by a change in composition constituting a welded portion or the like, most of the responses are echoes of reflected waves from a bottom surface, an edge, or a corner of the object to be tested 13. These echoes are collectively called shape echo Uc. To detect and evaluate the defect D, the defect echo Ud needs to be separated from the shape echo Uc.

When the low-frequency/high-frequency ultrasonic wave enters the object to be tested 13 to propagate over the entire surface and the entire inner portion thereof, the harmonic component Uh of the incident ultrasonic wave Ui is also generated in a transducer of the ultrasonic transmitting mechanism 14, a propagation medium, or a contact interface where the defect D is not supposed to exist. Thus, the harmonic component Uh is also detected from the shape echo Uc. However, the generating mechanism of the harmonics Uh appearing in the defect echo Ud depends on the defect D as described above. Accordingly, the harmonics Uh have a different generation efficiency from that of the nonlinear ultrasonic component of the originally-generated shape echo Uc.

Figure 25:
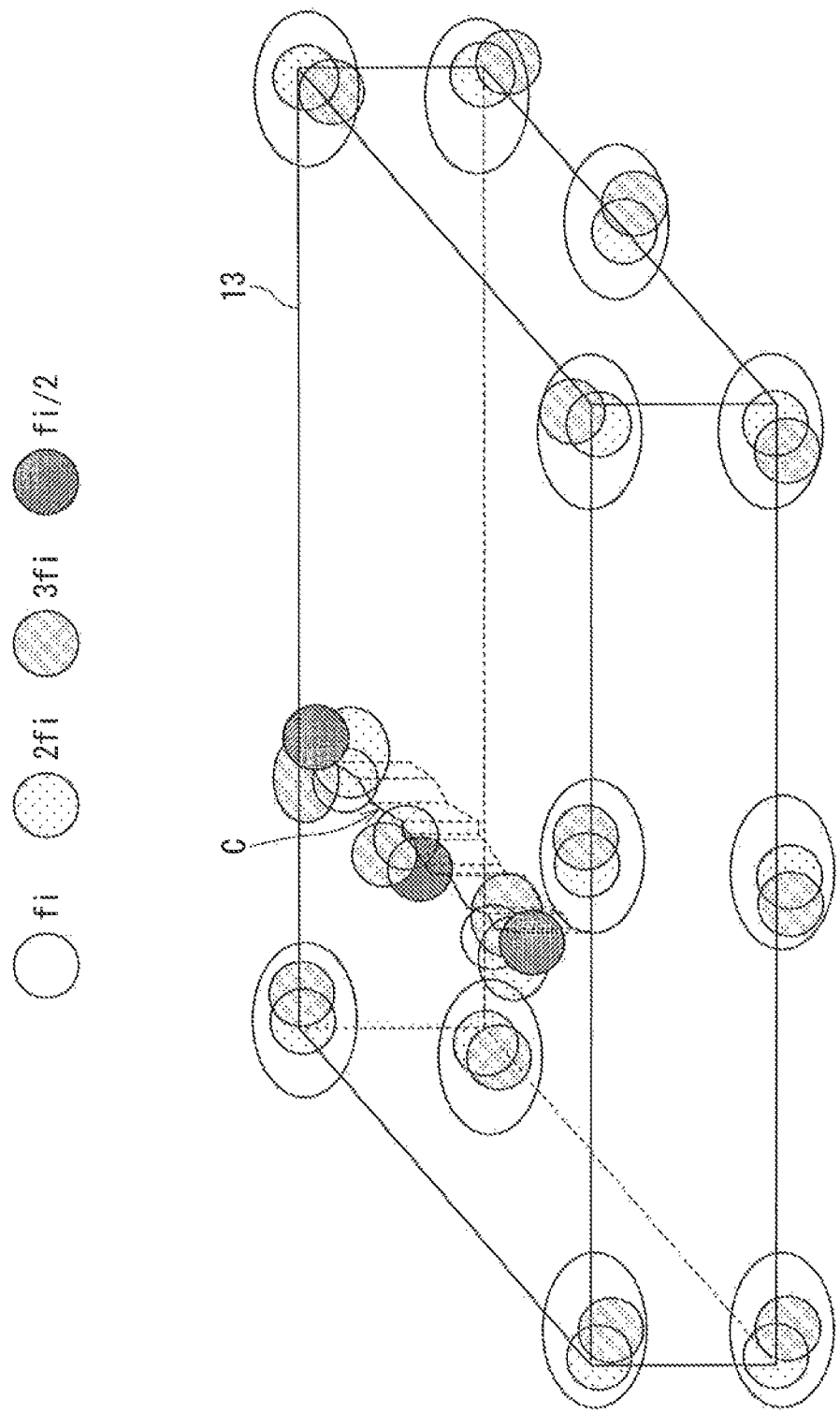
FIG. 25 is a schematic view illustrating the shape of the object to be tested, and a position property of the ultrasonic echo from the defect.

The subharmonics Us are known to be generated only by an interaction between the defect D and the ultrasonic wave. The respective echo sources can be identified as shown in FIG. 25 by performing the inverse problem analysis such as the inverse fast Fourier transform (IFFT) in the calculating mechanism 43 by using the waveform of the received ultrasonic wave Ur received at a plurality of points. The harmonic components or subharmonic components of the nonlinear ultrasonic wave are expressed differently between the defect echo Ud and the shape echo Uc of the object to be tested 13 as shown in FIG. 25.

Figure 26:
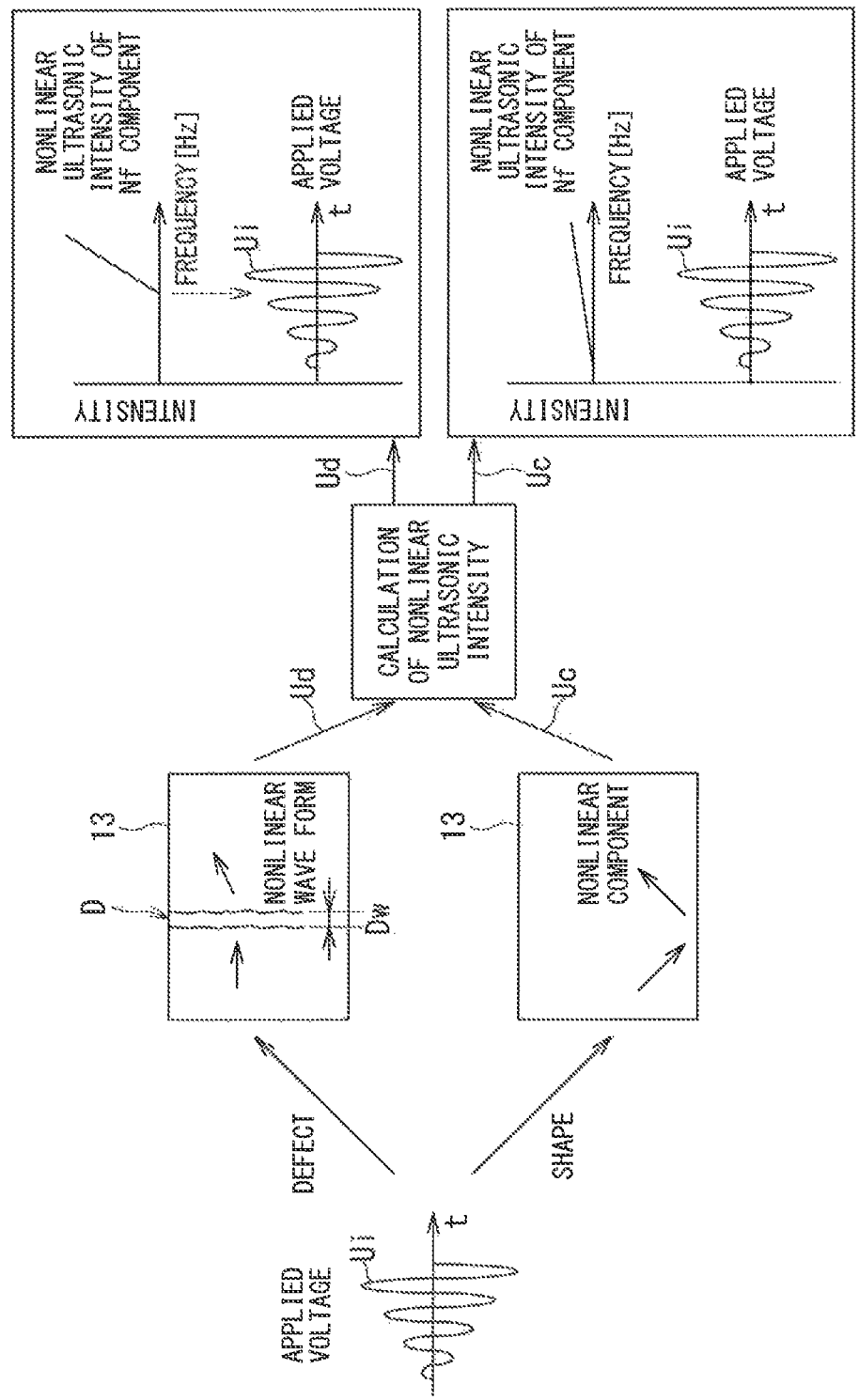
FIG. 26 is an explanatory view for explaining a difference in nonlinear ultrasonic intensity between a defect echo and a shape echo from the object to be tested.

In FIG. 25, respective patterns in circles indicate the frequencies of the first-order, second-order, and third-order harmonics Uh and the subharmonics Us, and the sizes thereof indicate the intensities of the harmonics Uh and the subharmonics Us. The source of the shape echo Uc is positioned at a corner portion and in a portion of a side of the object to be tested 13 for the sake of convenience. Of course, the echo may be generated from a bottom surface or any other sources. In the defect echo Ud and the shape echo Uc, the generation efficiencies of the nonlinear ultrasonic components are different from each other. A difference between the defect echo Ud and the shape echo Uc can be identified by comparing the generation efficiencies of the nonlinear ultrasonic components {the nonlinear ultrasonic intensities (scale intensities) of the harmonic (Nf) components} as shown in FIG. 26.

In general, the defect echo Ud has a larger nonlinear ultrasonic intensity (generation efficiency) of the harmonic (or subharmonic) Nf component than the shape echo Uc. In the defect echo Ud, when the incident amplitude Ai exceeds a certain threshold value, the nonlinear ultrasonic intensity of the harmonic Nf component rapidly rises. On the other hand, in the case of the shape echo Uc, the nonlinear ultrasonic intensity of the harmonic if component changes so as to linearly increase in proportion to the magnitude of the incident amplitude Ai.

In the ultrasonic test equipment 10F of the seventh embodiment, the signal generating mechanism 11 includes the modulating mechanism that temporally changes the amplitude of the (analog) voltage waveform signal generated therein. The control mechanism 17 is provided with a calculating function to synchronize the temporal change in the amplitude of the voltage waveform signal by the applied voltage and the intensity change in the nonlinear ultrasonic component obtained by the variation extracting mechanism 45, and obtain a relationship between the amplitude of the (analog) voltage waveform signal and a generation timing of the nonlinear ultrasonic component.

With the calculating function, the control mechanism 17 can distinguish the defect echo Ud and the shape echo Uc of the object to be tested 13 based on the difference in the nonlinear ultrasonic intensity, and can obtain the physical quantities of the defect D such as the opening width Dw of the defect D.

Effect of Seventh Embodiment

The ultrasonic test equipment 10F of the seventh embodiment uses the low-frequency and large-amplitude ultrasonic wave as the incident ultrasonic wave Ui on the object to be tested 13. The incident ultrasonic wave Ui has a low directionality and has a low propagation attenuation rate. Thus, the physical quantities such as the position, length, depth, and opening width of the defect in the object 13 can be quantitatively evaluated.

In the detection and evaluation of the defect in the object to be tested 13, it is focused that the generation efficiencies (intensities) of the nonlinear ultrasonic components differ between the defect echo Ud from the defect and the shape echo Uc from positions other than the defect included in the digital ultrasonic waveform from the AD converting mechanism 19. The echo source is identified by performing the inverse problem analysis in the calculating mechanism 43 by the use of the received digital ultrasonic waveform.

Since the generation efficiencies of the nonlinear ultrasonic components differ between the shape echo Uc and the defect echo Ud, the difference between the shape echo Uc and the defect echo Ud can be identified by comparing the generation efficiencies of the nonlinear ultrasonic components. Accordingly, the physical quantities such as the position, the length Dl, the depth Da, and the opening width Dw of the defect D can be extensively and nondestructively detected.

Although the present embodiment has been described as the configuration in which the signal processor 16A is used instead of the signal processor 16 of the first embodiment and the display mechanism 40 is added thereto, the signal processor 16A and the display mechanism 40 may be also applied to the respective first to sixth embodiments and the modifications thereof.

Eighth Embodiment

Next, an eighth embodiment of the ultrasonic test equipment is described by using FIGS. 23 to 26.

Since an entire system configuration of an ultrasonic test equipment 10G of the eighth embodiment is not different from that of the ultrasonic test equipment 10F of the seventh embodiment, the same components and operations are assigned with the same reference numerals, and overlapping description is omitted.

In the ultrasonic test equipment 10G of the eighth embodiment, the signal generating mechanism 11 includes a modulating device that forms a modulation wave by temporally changing the amplitude of the analog voltage (waveform) signal generated therein. The variation extracting mechanism 45 of the signal processor 16A calculates a temporal change in the intensity (generation efficiency) of a specific nonlinear ultrasonic component extracted therein. The control mechanism 17 includes a calculating mechanism that obtains the relationship between the generation timing of the nonlinear ultrasonic component and the analog voltage waveform signal by inputting the temporal change in the amplitude of the analog voltage (waveform) signal and the intensity change in the nonlinear ultrasonic component extracted by the variation extracting mechanism 45, and synchronizing the intensity change in the nonlinear ultrasonic component with the analog voltage waveform signal from the signal generating mechanism 11.

The calculating mechanism has a function to distinguish the defect echo Ud and the shape echo Uc and calculate the physical quantities such as the opening width Dw of the defect D.

Although the example in which the signal generating mechanism 11 forms the modulation wave by temporally changing the amplitude of the analog voltage (waveform) signal has been described in the ultrasonic test equipment 10G of the eighth embodiment, any type of modulating device may be employed as long as the device can temporally change the intensity of the entering ultrasonic signal by, for example, changing the frequency of a sinusoidal burst wave as the analog voltage waveform signal so as to enable quantitative evaluation.

Operation and Effect of Eighth Embodiment

In the ultrasonic test equipment 10G of the eighth embodiment, the generation efficiency of the nonlinear ultrasonic wave (the nonlinear ultrasonic intensity) in the defect echo Ud changes depending on the incident frequency fi and the incident amplitude Ai of the incident ultrasonic wave Ui, the defect length Dl, the defect depth Da, the defect opening width Dw, and the stress state Dp applied to the defect as shown in FIG. 26 (FIGS. 10A and 10B, FIGS. 11A and 11B). Therefore, when the incident, amplitude Ai of the incident ultrasonic wave Ui is equal to or less than a certain level (threshold value), and the defect length Dl, the defect depth Da, the defect opening width Dw, and the stress state Dp applied to the defect are equal to or less than a certain level, the nonlinear ultrasonic wave is not generated in the defect echo Ud (see a right upper portion in FIG. 26).

The nonlinear ultrasonic component in the shape echo Uc does not depend on the incident amplitude Ai, but is considered to be included in the shape echo Uc at a certain rate depending on ultrasonic wave incident conditions from the ultrasonic transmitting mechanism 14 (14A), shape conditions of the object to be tested 13, or the like. Therefore, a signal in which the nonlinear ultrasonic component is generated at a certain timing against the incident amplitude Ai is expressed as a signal in which the nonlinear ultrasonic intensity of the harmonic Nf component continuously changes, and the nonlinear ultrasonic signal can be determined as the shape echo Uc (see FIG. 26).

In the control mechanism 17, the calculating mechanism 43 obtains the relationship between the generation timing of the nonlinear ultrasonic component and the amplitude of the analog voltage waveform signal by the calculations based on the change in the amplitude of the analog voltage waveform signal and the temporal change in the intensity of the nonlinear ultrasonic component from the variation extracting mechanism 45.

Accordingly, the control mechanism 17 can distinguish the defect echo Ud and the shape echo Uc of the object to be tested 13 based on the difference in the nonlinear ultrasonic intensity by using the temporal change in the amplitude of the voltage waveform signal and the generation timing of the nonlinear ultrasonic component from the variation extracting mechanism 45. The control mechanism 17 can thereby obtain the physical quantities such as the opening width Dw of the defect D by calculations.

In the ultrasonic test equipment 10G of the eighth embodiment, the signal generating mechanism 11 may be provided with a function of generating a sinusoidal burst wave as the voltage waveform signal instead of the function of temporally changing the amplitude of the analog voltage waveform signal. The control mechanism 17 controls the frequency of the burst wave from the signal generating mechanism 11, and distinguishes the defect echo Ud and the shape echo Uc based on the difference in the nonlinear ultrasonic intensity by using the frequency of the burst wave and the frequency of the burst wave obtained when the nonlinear ultrasonic component is generated from the variation extracting mechanism 45. The control mechanism 17 can thereby obtain the opening width Dw of the defect D by calculations.

Although some of the embodiments of the present invention have been described hereinbefore, these embodiments are merely examples, and not intended to limit the scope of the invention. These novel embodiments can be carried out in various other forms, and may be omitted, replaced, changed, or combined without departing from the spirit of the invention. These embodiments and the modifications thereof are included in the scope and spirit of the invention and also included in the scope of the invention described in claims and a range equivalent thereto.

For example, although the ultrasonic transmitting mechanism and the ultrasonic receiving mechanism are separately installed in the respective embodiments, the ultrasonic transmitting mechanism and the ultrasonic receiving mechanism may be respectively composed of electromagnetic or piezoelectric ultrasonic transducers, or may be composed of a single ultrasonic transducer capable of transmitting and receiving ultrasonic waves.

What is claimed is:

1. An ultrasonic test equipment comprising:
    a signal generating mechanism that generates a voltage waveform;
    an ultrasonic transmitting mechanism that excites ultrasonic vibrations having a lower frequency than a predetermined frequency to an object to be tested;
    an ultrasonic receiving mechanism that receives an ultrasonic response from the object to be tested;
    an AD converting mechanism that digitizes the received ultrasonic waveform;
    an analyzing mechanism that performs frequency analysis of the digital ultrasonic waveform digitized by the AD converting mechanism;
    an evaluating mechanism that extracts a variation of a nonlinear ultrasonic component from a frequency component of the digital ultrasonic wave obtained by the frequency analysis, compares the variation with defect data information in a defect information database, identifies a physical quantity of defect information of the object to be tested, and evaluates a defect in the object to be tested; and
    a control mechanism that partly or entirely controls a measurement system.

2. The ultrasonic test equipment according to claim 1, wherein at least one of the ultrasonic transmitting mechanism and the ultrasonic receiving mechanism includes a plurality of ultrasonic transmitting mechanisms or a plurality of ultrasonic receiving mechanisms and a recording device that records a reference waveform obtained from an object to be tested with no defect,
    wherein the analyzing mechanism performs correlation processing between the digital ultrasonic waveform obtained from the ultrasonic receiving mechanism through the AD converting mechanism and a signal obtained from the reference waveform, and, performs a removal process of removing, from the digital ultrasonic waveform, a signal with the reference waveform exhibiting a correlation equal to or more than a predetermined value in the correlation processing, and the analyzing mechanism identifies a defect position based on a characteristic ultrasonic signal of the digital ultrasonic waveform after the removal process.

3. The ultrasonic test equipment according to claim 1, wherein at least one of the ultrasonic transmitting mechanism and the ultrasonic receiving mechanism includes a scanning mechanism that moves a plurality of ultrasonic transmitting mechanisms or ultrasonic receiving mechanisms relative to each other,
    wherein the analyzing mechanism includes a position identifying device that identifies a defect position by performing correlation processing between the digital ultrasonic waveform obtained from the ultrasonic receiving mechanism through the AD converting mechanism and a reference ultrasonic signal obtained from a reference waveform of an object to be tested with no defect.

4. The ultrasonic test equipment according to claim 1, wherein the analyzing mechanism analyzes a generation efficiency of the nonlinear ultrasonic component from the frequency component of the digital ultrasonic waveform obtained from the ultrasonic receiving mechanism through the AD converting mechanism, and the evaluating mechanism is configured to achieve a function to acquire at least one of physical quantities of a length, a depth, an opening width, and an opening stress of the defect in the object to be tested by matching frequency information of the analyzed digital ultrasonic waveform with known defect data information in the defect information database.

5. The ultrasonic test equipment according to claim 1, wherein the signal generating mechanism is configured to achieve a function to sweep a frequency of the voltage waveform, the analyzing mechanism analyzes a tendency of a generation efficiency of the nonlinear ultrasonic component in response to a frequency change in the digital ultrasonic waveform obtained from the ultrasonic receiving mechanism through the AD converting mechanism, and the evaluating mechanism is configured to achieve a function to acquire at least one of physical quantities of a length, a depth, an opening width, and an opening stress of the defect in the object to be tested by matching frequency information of the analyzed digital ultrasonic waveform with known defect data information in the defect information database.

6. The ultrasonic test equipment according to claim 1, wherein the signal generating mechanism has a function to generate the voltage waveform having a plurality of mixed frequencies, the analyzing mechanism analyzes a tendency of a generation efficiency of the nonlinear ultrasonic component in response to a frequency change in the digital ultrasonic waveform obtained from the ultrasonic receiving mechanism through the AD converting mechanism, and the evaluating mechanism is configured to achieve a function to acquire at least one of physical quantities of a length, a depth, an opening width, and an opening stress of the defect in the object to be tested by matching frequency information of the analyzed digital ultrasonic waveform with known defect data information in the defect information database.

7. The ultrasonic test equipment according to claim 1, wherein the ultrasonic receiving mechanism is composed of a hydrophone and uses only an ultrasonic component leaking into water from the defect in the object to be tested for analysis.

8. The ultrasonic test equipment according to claim 1, wherein a remote viewing camera is used to observe a same range as a flaw detection range of the object to be tested, and the defect information of the object to be tested is superimposed on an image obtained by the remote viewing camera and displayed.

9. The ultrasonic test equipment according to claim 1, wherein an acoustic impedance matching layer that improves an ultrasonic propagation efficiency is provided between at least one of the ultrasonic transmitting mechanism and the ultrasonic receiving mechanism, and the object to be tested.

10. A method for evaluating a test result by an ultrasonic test equipment, comprising the steps of:
    transmitting an ultrasonic wave having a low frequency lower than a predetermined frequency to an object to be tested;
    receiving an ultrasonic response from the object to be tested by an ultrasonic receiving mechanism;
    converting the received analog ultrasonic waveform to a digital ultrasonic waveform;
    performing frequency analysis of the converted digital ultrasonic waveform by an analyzing mechanism; and
    extracting a variation of a nonlinear ultrasonic component from frequency information of the digital ultrasonic waveform of the object to be tested obtained by the frequency analysis, matching the variation with known defect data information in a defect information database, identifying a physical quantity of defect information of the object to be tested, and then, evaluating a defect in the object to be tested by an evaluating mechanism.

11. An ultrasonic test equipment comprising:
    a signal generating mechanism that generates a voltage waveform;
    an ultrasonic transmitting mechanism that excites ultrasonic vibrations having a lower frequency than a predetermined frequency to an object to be tested;
    an ultrasonic receiving mechanism that receives an ultrasonic response from the object to be detected;
    an AD converting mechanism that digitizes the received ultrasonic waveform;
    a calculating mechanism that performs an inverse problem calculation of a spatial intensity distribution from the digitized ultrasonic waveform;
    a filtering mechanism that calculates the spatial intensity distribution filtered by any frequency component;
    a variation extracting mechanism that extracts an intensity variation of a nonlinear ultrasonic component;
    a display mechanism that displays at least the filtered spatial intensity distribution from the filtering mechanism; and
    a control mechanism that partly or entirely controls a measurement system.

12. The ultrasonic test equipment according to claim 11, wherein the signal generating mechanism is configured to achieve a function to temporally change an amplitude of the voltage waveform signal, and the control mechanism is configured to achieve a function to distinguish a defect echo Ud and a shape echo Uc based on the change in the amplitude of the voltage waveform signal, and a generation timing of the nonlinear ultrasonic component from the variation extracting mechanism.

13. The ultrasonic test equipment according to claim 11,
    wherein the signal generating mechanism has a function to temporally change an amplitude of the voltage waveform signal, and
    the control mechanism has a function to calculate an opening width of the defect based on the change in the amplitude of the voltage waveform signal, and a generation timing of the nonlinear ultrasonic component from the variation extracting mechanism.

14. The ultrasonic test equipment according to claim 11, wherein the signal generating mechanism has a function to generate a sinusoidal burst wave as the voltage waveform signal, and the control mechanism has a function to control a frequency of the burst wave, and distinguish a defect echo Ud and a shape echo Uc based on the frequency of the burst wave, and the frequency of the burst wave obtained when the nonlinear ultrasonic component is generated from the variation extracting mechanism.

15. The ultrasonic test equipment according to claim 11, wherein the signal generating mechanism is configured to achieve a function to generate a sinusoidal burst wave as the voltage waveform signal, and the control mechanism is configured to achieve a function to control a frequency of the burst wave, and calculate an opening width of the defect based on the frequency of the burst wave, and the frequency of the burst wave obtained when the nonlinear ultrasonic component is generated from the variation extracting mechanism.

* * * * *